US010711064B2

(12) United States Patent
Epstein

(10) Patent No.: US 10,711,064 B2
(45) Date of Patent: Jul. 14, 2020

(54) LYM-1 AND LYM-2 TARGETED CAR CELL IMMUNOTHERAPY

(71) Applicant: Alan L. Epstein, Pasadena, CA (US)

(72) Inventor: Alan L. Epstein, Pasadena, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 15/173,534

(22) Filed: Jun. 3, 2016

(65) Prior Publication Data
US 2016/0355590 A1 Dec. 8, 2016

Related U.S. Application Data

(60) Provisional application No. 62/171,004, filed on Jun. 4, 2015.

(51) Int. Cl.
C07K 16/28 (2006.01)
C07K 16/30 (2006.01)
C07K 14/725 (2006.01)
C07K 14/705 (2006.01)
A61K 39/395 (2006.01)
G01N 33/574 (2006.01)
A61K 39/00 (2006.01)

(52) U.S. Cl.
CPC .... *C07K 16/2833* (2013.01); *A61K 39/39558* (2013.01); *C07K 14/7051* (2013.01); *C07K 14/70517* (2013.01); *C07K 14/70521* (2013.01); *C07K 14/70578* (2013.01); *A61K 2039/505* (2013.01); *C07K 2317/565* (2013.01); *C07K 2317/622* (2013.01); *C07K 2317/73* (2013.01); *C07K 2317/92* (2013.01); *C07K 2319/02* (2013.01); *C07K 2319/03* (2013.01); *C07K 2319/33* (2013.01); *G01N 33/57492* (2013.01); *G01N 2333/70539* (2013.01); *G01N 2800/52* (2013.01)

(58) Field of Classification Search
IPC .................. C07K 2319/00,16/2833, 14/70521, 2319/33; A61K 39/39558, 51/1069
See application file for complete search history.

(56) References Cited

U.S. PATENT DOCUMENTS

| 4,724,212 | A | 2/1988 | Epstein |
| 4,724,213 | A | 2/1988 | Epstein |
| 7,892,753 | B1 | 2/2011 | Banerjee |
| 8,580,257 | B2 | 11/2013 | Tremblay et al. |
| 2005/0208048 | A1 | 9/2005 | McMahan et al. |
| 2006/0063209 | A1 | 3/2006 | Meares et al. |
| 2013/0287748 | A1 | 10/2013 | June et al. |
| 2014/0241984 | A1 | 8/2014 | El-Agnaf |
| 2014/0370017 | A1 | 12/2014 | June et al. |
| 2015/0017141 | A1 | 1/2015 | June et al. |
| 2015/0118202 | A1 | 4/2015 | June et al. |

FOREIGN PATENT DOCUMENTS

| CN | 104159917 A | 11/2014 | |
| WO | WO-2004/081199 A2 | 9/2004 | |
| WO | WO-2007/058725 A2 | 5/2007 | |
| WO | WO-2010/060186 A1 | 6/2010 | |
| WO | WO-2015/133817 A1 | 9/2015 | |
| WO | WO-2016/160618 A2 | 10/2016 | |
| WO | WO2016/174652 | * 11/2016 | ............. A61K 48/00 |
| WO | WO-2018/154386 A1 | 8/2018 | |

OTHER PUBLICATIONS

Inaguma et al., Construction and molecular characterization of a T-cell receptor-like antibody and CAR-T cells specific for minor histocompatibility antigen HA-1H. Gene Therapy (2014) 21, 575-584.*
Rose et al., Lymphoma-selective antibody Lym-1 recognizes a discontinuous epitope on the light chain of HLA-DR10. Cancer Immunol Immunother (1996) 43: 26-30.*
Wellman et al., Sequences of the Lym-1 antibody heavy and light chain variable regions. Nucleic Acids Research, vol. 18, No. 17 5281.*
Paul, Fundamental Immunology, 3rd Edition, 1993, pp. 292-295 (Year: 1993).*
Rudikoff et al. (Proceedings of the National Academy of Sciences USA, vol. 79, p. 1979, 1982 (Year: 1982).*
Panka et al. (Proceedings of the National Academy of Sciences USA, vol. 85, 1988 (Year: 1988).*
International Search Report and Written Opinion, issued in PCT/US2016/035916.
International Preliminary Report on Patentability dated Dec. 14, 2017, from application No. PCT/US2016/035916.
Anonymous, "Immunotherapy—MVR-CAR", Sep. 10, 2013 (Sep. 10, 2013), XP055528952, Retrieved from the Internet: URL:https://www.google.de/url?sa=t&rct=j&q=&esrc=s&source=web&cd=14&ved=2ahUKEwiZI46N5Pv eAhUJJ1AKHYlpAHMQFjANegQIAhAC&url=http%3A%2F%2Fedu.ncc.re.kr%2Fdownload%3Ffn%3D 2013%2F9% F1588828777125444.pdf, p. 49-p. 52.
Chungyong Han et al, "Desensitized chimeric antigen receptor T cells selectively recognize target cells with enhanced antigen expression", Nature Communications, vol. 9, No. 1, Feb. 1, 2018 (Feb. 1, 2018), XP055528807, DOI: 10.1038/541467-018-02912-x.
Chungyong Han et al, "Impact of the affinity of chimeric antigen receptor on immune activation profiles of T cells Cancer Research", Jul. 1, 2018 (Jul. 1, 2018), XP055528821, Retrieved from the Internet: URL:http://cancerres.aacrjournals.org/content/78/13_Supplement/3563.
Chungyong Han et al, "Selective killing of malignant B cells using T cells redirected against malignancy variant receptor", Journal for Immunotherapy of Cancer, Biomed Central Ltd, London, UK, vol. 2, No. Suppl 3, Nov. 6, 2014 (Nov. 6, 2014), p. P16, XP021202422, ISSN: 2051-1426, DOI: 10.1186/2051-1426-2-S3-P16.

(Continued)

*Primary Examiner* — Christopher M Babic
*Assistant Examiner* — Arthur S Leonard
(74) *Attorney, Agent, or Firm* — Foley & Lardner LLP; Antoinette F. Konski

(57) ABSTRACT

CAR cells targeting and antibodies human HLA-DR are described as a new method of cancer treatment. It is proposed that HLA-DR CAR cells are safe and effective in patients and can be used to treat human tumors expressing the HLA-DR.

16 Claims, 13 Drawing Sheets

Specification includes a Sequence Listing.

(56) References Cited

OTHER PUBLICATIONS

Epstein A L et al, "Two New Monoclonal Antibodies, LYM-1 and LYM-2, Reactive With Humanb-Lymphocytes and Derived Tumors, with Immunodiagnostic and Immunotherapeutic Potential", Cancer Research, & 102nd Annual Meeting of the American-Association-For-Cancer-Research (AACR); Orlando, FL, USA; Apr. 2-6, 2011, vol. 47, No. 2, Feb. 1, 1987 (Feb. 1, 1987), pp. 830-840, XP000121069, ISSN: 0008-5472.
Extended European Seach Report dated Jan. 22, 2019, from application No. 1604607.6.
Long Zheng et al, "Lym-1 Chimeric Antigen Receptor T Cells Exhibit Potent Anti-Tumor Effects against B-Cell Lymphoma", International Journal of Molecular Sciences, vol . 18, No. 12, Dec. 20, 2017 (Dec. 20, 2017), p. 2773, XP055528773, DOI: 10.3390/ijms18122773.
Sally J Denardo et al, "67Cu-21T-BAT-Lym1-Pharmacokinetics, Radiation Dosimetry, Toxicity and Tumor Regression in Patients with Lymphoma", J Nucl Med 40(2), Feb. 1, 1999 (Feb. 1, 1999), pp. 302-310, XP055528924, Retrieved from the Internet: URL:http://jnm.snmjournals.org/content/40/2/302.full.pdf.
Arias, et al. "RA8, A Human Anti-CD25 Antibody Against Human Treg Cells", Hybridoma, 2007, vol. 26, No. 3, pp. 119-130.
Colman et al Effects of amino acid sequence changes on antibody-antigen interactions Research in Immunology, 145:33-36, 1994.
Database Medline [Online] US National Library of Medicine (NLM), Bethesda, MD, US; Nov. 2003 (Nov. 2003), Funaro Ada et al: "Functional, structural, and distribution analysis of the chorionic gonadotropin receptor using murine monoclonal antibodies.", XP002783240, Database accession No. NLM14602802, *abstract* & Funaro Ada et al: "Functional, structural, and distribution analysis of the chorionic gonadotropin receptor using murine monoclonal antibodies", the Journal of Clinical Endocrinology A.
Kennell et al., Principles and Practices of Nucleic Acid Hybridization Progress in Nucleic Acid Research and Molecular Biology vol. 11, 1971, pp. 259-301.
U.S. Appl. No. 16/335,570, filed Sep. 22, 2017, University of Southern California.
Kumar, et al., "Critical role of OX40 signaling in the TCR-independent phase of human and murine thymic Treg generation", Cellular and Molecular Immunology, 2019, 16, pp. 138-153.
Li, et al. "Complete Regression of Experimental Solid Tumors by Combination LEC/chTNT-3 Immunotherapy and CD25 T-cell Depletion", Cancer Research, Dec. 1, 2003, 63, pp. 8384-8392.
McKay Brown et al, "Tolerance to single, but not multiple, amino acid replacements in antibody V-H CDR2: A means of minimizing B cell wastage from somatic hypermutation?", The Journal of Immunology, The American Association of Immunologists, US, vol. 156, No. 9, Jan. 1, 1996 (Jan. 1, 1996), pp. 3285-3291, XP002649029, ISSN: 0022-1767.
Niedojadlo, et al., "The perichromatin region of the plant cell nucleus is the area with the strongest co-localisation of snRNA and SR proteins", Planta, 2012, 236, pp. 715-726.
Single-chain variable fragment—Wikipedia Single-chain variable fragment pp. 1-3, downloaded Oct. 2, 2019.
Winkler K et al, "Changing the antigen binding specificity by single point mutations of an anti-p24 (HIV-1) antibody", The Journal of Immunology, The American Association of Immunologists, US, vol. 165, No. 8, Oct. 15, 2000 (Oct. 15, 2000), pp. 4505-4514, XP002579393, ISSN: 0022-1767.
Zhang, et al. "Lym-1-Induced Apoptosis of Non-Hodgkin's Lymphomas Produces Regression of Transplanted Tumors", Cancer Biotherapy & Radiopharmaceuticals, vol. 22, No. 3, 2007, pp. 342-356.
Dotti, et al., "Design and Development of Therapies using Chimeric Antigen Receptor-Expressing T cells", Immunol. Rev., Jan. 2014; 257(1)pp. 1-35.
MacCallum, et al., "Antibody-antigen Interactions: Contact Analysis and Binding Site Topography", J. Mol. Biol., (1996) 262, pp. 732-745.

* cited by examiner

LYM-1 AND LYM-2 TARGETED CAR CELL IMMUNOTHERAPY

CROSS-REFERENCE TO RELATED APPLICATION

This application claims priority under 35 U.S.C. § 119(e) to U.S. Provisional Application No. 62/171,004, filed Jun. 4, 2015, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 1, 2016, is named 064189-7201_SL.txt and is 51,805 bytes in size.

BACKGROUND

The present disclosure relates generally to the field of human immunology, specifically cancer immunotherapy.

The following discussion of the background is merely provided to aid the reader in the understanding the disclosure and is not admitted to describe or constitute prior art to the present disclosure.

Lym-1 and Lym-2 are directed against MHC class II HLA-DR molecules which are primarily expressed on the surface of human B cells, dendritic cells, and B-cell derived lymphomas and leukemias.

SUMMARY

Provided are methods and compositions relating to new cancer immunotherapeutic chimeric antigen receptors (CARs). Aspects of the disclosure relate to a chimeric antigen receptor (CAR) comprising, or alternatively consisting essentially of, or yet further consisting of: (a) an antigen binding domain of a Lym-1 and/or Lym-2 antibody; (b) a hinge domain; (c) a transmembrane domain; and (d) an intracellular domain. Further aspects of the disclosure relate to a chimeric antigen receptor (CAR) comprising, or alternatively consisting essentially of, or yet further consisting of: (a) an antigen binding domain of a Lym-1 and/or Lym-2 antibody; (b) a CD8 α hinge domain; (c) a CD8 α transmembrane domain; (d) a CD28 costimulatory signaling region and/or a 4-1BB costimulatory signaling region; and (e) a CD3 zeta signaling domain.

Aspects of the disclosure relate to Lym-1 and Lym-2 antibodies.

Some aspects of the disclosure relate to a chimeric antigen receptor (CAR) comprising an antigen binding domain specific to human HLA-DR antigens—for example, the antigen binding domain of Lym-1 and Lym-2 antibodies.

Further aspects of the disclosure relate to an isolated nucleic acid sequence encoding a Lym1 or Lym-2 CARs and vectors comprising the isolated nucleic acid sequences.

Other aspects of the disclosure relate to an isolated cell comprising a Lym-1 or Lym-2 directed CAR and methods of producing such cells. Still other method aspects of the disclosure relate to methods for inhibiting the growth of a tumor and treating a cancer patient comprising, or alternatively consisting essentially of, or yet further consisting of, administering an effective amount of the isolated cell to a tissue or subject in need of such.

Further method aspects of the disclosure relate to methods for determining if a patient is likely or unlikely to respond to Lym-1 CAR or Lym-2 CAR therapy through use of one or more of the Lym-1 or Lym-2 antibodies and/or the Lym-1 CAR or Lym-2 CAR cells.

Additional aspects of the disclosure relate to compositions comprising a carrier and one or more of the products described in the embodiments disclosed herein.

BRIEF DESCRIPTION OF THE DRAWINGS

(FIG. 1B) Lym-1; (FIG. 1C) Lym-1 and B1; (FIG. 1D) B1 only; (FIG. 1E) Lym-2; and (FIG. 1F) Lym-2 and B1 staining reactivity with normal peripheral blood lymphocytes of patients. Both Lym-1 and Lym-2 have different profiles of binding to normal human peripheral B cells.

(FIG. 4B) Scatchard plot analysis of Lym-1 monoclonal antibodies with Raji cells; (FIG. 4C) Scatchard plot analysis of Lym-2 monoclonal antibodies with ARH-77 cells.

FIGS. 6A and 6B disclose SEQ ID NO: 51.

DETAILED DESCRIPTION

Figures 1A, 1B, 1C, 1D, 1E, 1F:
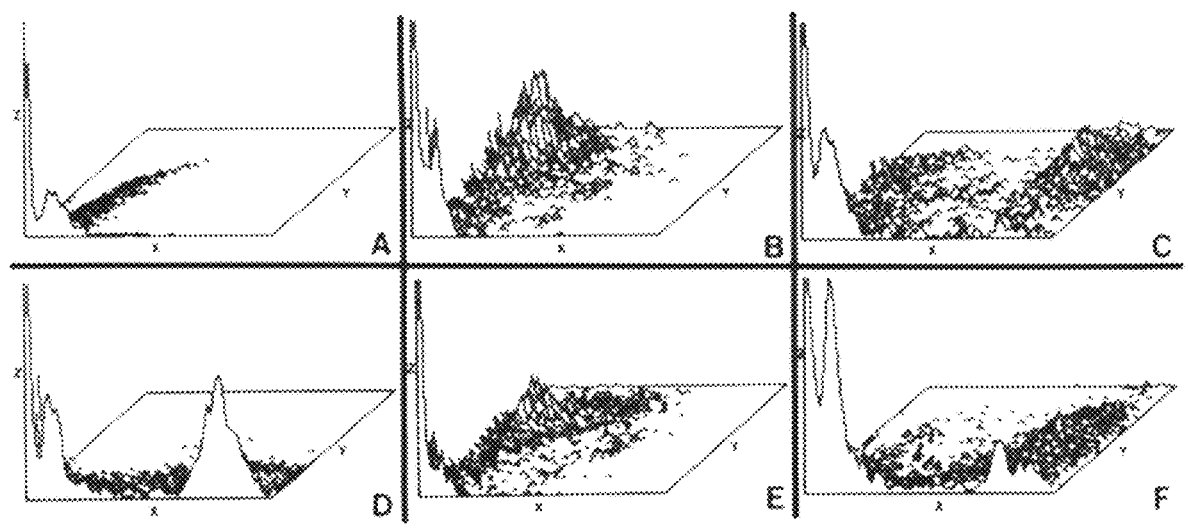
FIGS. 1A-1F show flow cytometric analysis of (FIG. 1A) negative control.

It is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the preferred methods, devices and materials are now described. All technical and patent publications cited herein are incorporated herein by reference in their entirety. Nothing herein is to be construed as an admission that the present technology is not entitled to antedate such disclosure by virtue of prior invention.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the present technology relates to a polypeptide, protein, polynucleotide or antibody, an equivalent or a biologically equivalent of such is intended within the scope of the present technology.

Definitions

As used in the specification and claims, the singular form "a", "an", and "the" include plural references unless the context clearly dictates otherwise. For example, the term "a cell" includes a plurality of cells, including mixtures thereof.

As used herein, the term "animal" refers to living multicellular vertebrate organisms, a category that includes, for example, mammals and birds. The term "mammal" includes both human and non-human mammals.

The terms "subject," "host," "individual," and "patient" are as used interchangeably herein to refer to human and veterinary subjects, for example, humans, animals, non-human primates, dogs, cats, sheep, mice, horses, and cows. In some embodiments, the subject is a human.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. Unless specifically noted otherwise, the term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4 M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook (1994-1995) (Pierce Chemical Co., Rockford, Ill.); Kuby, J. (1997) *Immunology*, $3^{rd}$ Ed., W.H. Freeman & Co., New York. An "antigen binding fragment" of an antibody is a portion of an antibody that retains the ability to specifically bind to the target antigen of the antibody.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies and human antibodies.

In terms of antibody structure, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopts a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located (heavy chain regions labeled CDHR and light chain regions labeled CDLR). Thus, a CDHR3 is the CDR3 from the variable domain of the heavy chain of the antibody in which it is found, whereas a CDLR1 is the CDR1 from the variable domain of the light chain of the antibody in which it is found. A TNT antibody will have a specific $V_H$ region and the $V_L$ region sequence unique to the TNT relevant antigen, and thus specific CDR sequences. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, the term "antigen binding domain" refers to any protein or polypeptide domain that can specifically bind to an antigen target.

The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell. In certain embodiments, the intracellular domain may comprise, alternatively consist essentially of, or yet further comprise one or more costimulatory signaling domains in addition to the primary signaling domain. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non limiting examples of such domains are provided herein, e.g.:

Hinge domain: IgG1 heavy chain hinge sequence,
SEQ ID NO: 42:
CTCGAGCCCAAATCTTGTGACAAAACTCACACATGCCCACCGTGCCCG Transmembrane domain: CD28 transmembrane region
SEQ ID NO: 43:
TTTTGGGTGCTGGTGGTGGTTGGTGGAGTCCTGGCTTGCTATAGCTTGCT

AGTAACAGTGGCCTTTATTATTTTCTGGGTG

Intracellular domain: 4-1BB co-stimulatory
signaling region, SEQ ID NO: 44:
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

Intracellular domain: CD28 co-stimulatory
signaling region, SEQ ID NO: 45:
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

Intracellular domain: CD3 zeta signaling region,
SEQ ID NO: 46:
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAA

As used herein, the term "HLA-DR" (refers to an MHC class II cell surface receptor associated with this name and any other molecules that have analogous biological function that share at least 80% amino acid sequence identity, preferably 90% sequence identity, or alternatively at least 95% sequence identity with any HLA-DR variant, including but not limited to any one of its several variants, including but not limited to HLA-DR serotypes DR1 to DR 75 comprising a combination of HLA-DRA and HLA-DRB haplotypes. Examples of the HLA-DR sequences are known in the art and non-limited examples of such are disclosed in Rose, L. M. et al. (1996) Cancer Immunol. Immunother. 43:26-30:

HLA-DRB1*1001 [DR10]
SEQ ID NO: 30
GDTRPRFLEEVKFECHFFNGTERVRLLERRVHNQEEYARYDSDVGEYRAV

TELGRPDAEYWNSQKDLLERRRAAVDTYCRHNYGVGESFTVQRRVQPKVT

VYPSKTQPLQHHNLLVCSVNGFYPGSIEVRWFRNGQEEKTGVVSTGLIQN

GDWTFQTLVMLETVPQSGEVYTCQVEHPSVMSPLTVEWRARSESAQSKML

SGVGGFVLGLLFLGAGLFIYFRNQKGHSGLPPTGFLS;

HLA-DRB3*0201 [DR52]
SEQ ID NO: 31
GDTRPRFLELLKSECHFFNGTERVRFLERHFHNQEEYARFDSDVGEYRAV

FELGRPDAEYWNSQKDLLEQKRGQVDNYCRHNYGVVESFTVQRRVHPQVT

VYPAKTQPLQHHNLLVCSVSGFYPGSIEVRWFRNGQEEKAGVVSTGLIQN

GDWTFQTLVMLETFPRSGEVYTCQVEHPSVTSPLTVEWSARSESAQSKML

SGVGGFVLGLLFLGAGLFIYFRNQKGHSGLQPTGFLS;

HLA-DRB1*0301 [DR17 (3)]
SEQ ID NO: 32
GDTRPRFLEYSTSECHFFNGTERVRYLDRYFHNQEENVRFDSDVGEFRAV

TELGRPDAEYWNSQKDLLEQKRGRVDNYCRHNYGVVESFTVQRRVHPKVT

VYPSKTQPLQHHNLLVCSVSGFYPGSIEVRWFRNGQEEKTGVVSTGLIQN

GDWTFQTLVMLETVPRSGEVYTCQVEHPSVTSPLTVEWRARSESAQSKML

SGVGGFVLGLLFLGAGLFIYFRNQKGHSGLQPRGFLS, as well as equivalents of each thereof.

Rose et al. also discloses an exemplary epitope to which an HLA-DR specific antibody may bind and therefore can serve as an immunogen for the generation of additional antibodies, monoclonal antibodies and antigen binding fragments of each thereof. The sequences associated with each of the listed reference(s) and GenBank Accession Numbers that correspond to the name HLA-DR or its equivalents including but not limited to the specified HLA-DR subtypes are herein incorporated by reference as additional non-limiting examples.

A "composition" typically intends a combination of the active agent, e.g., a CAR T cell or a CAR NK cell, an antibody, a compound, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term "consensus sequence" as used herein refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. The generation of consensus sequences has been subjected to intensive mathematical analysis. Various software programs can be used to determine a consensus sequence.

As used herein, the term "CD8 α hinge domain" refers to a specific protein fragment associated with this name and any other molecules that have analogous biological function that share at least 70%, or alternatively at least 80% amino acid sequence identity, or alternatively at least 90% sequence identity, or alternatively at least 95% sequence identity with the CD8 α hinge domain sequence as shown herein. The example sequences of CD8 α hinge domain for human, mouse, and other species are provided in Pinto, R. D. et al. (2006) Vet. Immunol. Immunopathol. 110:169-177. The sequences associated with the CD8 α hinge domain are provided in Pinto, R. D. et al. (2006) Vet. Immunol. Immunopathol. 110:169-177. Non-limiting examples of such include:

```
Human CD8 alpha hinge domain;
                              (SEQ ID NO: 33)
PAKPTTTPAPRPPTPAPTIASQPLSLRPEACRPAAGGAVHTRGLDFACDI
Y Mouse CD8 alpha hinge domain;
                              (SEQ ID NO: 34)
KVNSTTTKPVLRTPSPVHPTGTSQPQRPEDCRPRGSVKGTGLDFACDIY Cat CD8 alpha hinge domain;
                              (SEQ ID NO: 35)
PVKPTTTPAPRPPTQAPITTSQRVSLRPGTCQPSAGSTVEASGLDLSCDI
Y,
``` and equivalents of each thereof.

As used herein, the term "CD8 α transmembrane domain" refers to a specific protein fragment associated with this name and any other molecules that have analogous biological function that share at least 70%, or alternatively at least 80% amino acid sequence identity, or alternatively at least 90% sequence identity, or alternatively at least 95% sequence identity with the CD8 α transmembrane domain sequence as shown herein. The fragment sequences associated with the amino acid positions 183 to 203 of the human T-cell surface glycoprotein CD8 alpha chain (NCBI Reference Sequence: NP_001759.3), or the amino acid positions 197 to 217 of the mouse T-cell surface glycoprotein CD8 alpha chain (NCBI Reference Sequence: NP_001074579.1), and the amino acid positions 190 to 210 of the rat T-cell surface glycoprotein CD8 alpha chain (NCBI Reference Sequence: NP_113726.1) provide additional example sequences of the CD8 α transmembrane domain. The sequences associated with each of the listed NCBI are provided as follows:

```
     Human CD8 alpha transmembrane domain,
     (SEQ ID NO: 36):
     IYIWAPLAGTCGVLLLSLVIT;

Mouse CD8 alpha transmembrane domain,
     (SEQ ID NO: 37):
     IWAPLAGICVALLLSLIITLI;

Rat CD8 alpha transmembrane domain,
     (SEQ ID NO: 38):
     IWAPLAGICAVLLLSLVITLI,
``` and equivalents of each thereof.

As used herein, the term "4-1BB costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the 4-1BB costimulatory signaling region sequence as shown herein. The example sequences of the 4-1BB costimulatory signaling region are provided in U.S. Patent Application Publication No. 2013/0266551 A1 (filed as U.S. application Ser. No. 13/826,258). The sequence of the 4-1BB costimulatory signaling region associated disclosed in the U.S. application Ser. No. 13/826,258 is disclosed as follows:

```
The 4-1BB costimulatory signaling region (SEQ ID
NO: 39):
KRGRKKLLYIFKQPFMRPVQTTQEEDGCSCRFPEEEEGGCEL,
``` and equivalents of each thereof.

As used herein, the term "CD28 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD28 costimulatory signaling region sequence shown herein. The CD28 costimulatory region comprises an transmembrane domain and an intracellular domain. The example sequences CD28 costimulatory signaling domain are provided in U.S. Pat. No. 5,686,281; Geiger, T. L. et al. (2001) Blood 98:2364-2371; Hombach, A. et al. (2001) J Immunol. 167:6123-6131; Maher, J. et al. (2002) Nat Biotechnol. 20:70-75; Haynes, N. M. et al. (2002) J Immunol. 169:5780-5786; Haynes, N. M. et al. (2002) Blood 100:3155-3163. Non-limiting examples include residues 114-220 of the below CD28 Sequence, (SEQ ID NO: 40):

```
MLRLLLALNL FPSIQVTGNK ILVKQSPMLV AYDNAVNLSC

KYSYNLFSRE FRASLHKGLDSAVEVCVVYG NYSQQLQVYS

KTGFNCDGKL GNESVTFYLQ NLYVNQTDIY

FCKIEVMYPPPYLDNEKSNG TIIHVKGKHL CPSPLFPGPS

KPFWVLVVVG GVLACYSLLVTVAFIIFWVR SKRSRLLHSD

YMNMTPRRPG PTRKHYQPYA PPRDFAAYRS,
``` and equivalents thereof.

As used herein, the term "ICOS costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the ICOS costimulatory signaling region sequence as shown herein. Non-limiting example sequences of the ICOS costimulatory signaling region are provided in U.S. Publication 2015/0017141A1 the exemplary polynucleotide sequence provided below.

```
ICOS costimulatory signaling region, SEQ ID NO:
47:
ACAAAAAAGA AGTATTCATC CAGTGTGCAC GACCCTAACG

GTGAATACAT GTTCATGAGA GCAGTGAACA CAGCCAAAAA

ATCCAGACTC ACAGATGTGA CCCTA
```

As used herein, the term "OX40 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the OX40 costimulatory signaling region sequence as shown herein. Non-limiting example sequences of the OX40 costimulatory signaling region are disclosed in U.S. Publication 2012/20148552A1, and include the exemplary sequence provided below.

```
OX40 costimulatory signaling region, SEQ ID NO:
48:
AGGGACCAG AGGCTGCCCC CCGATGCCCA CAAGCCCCCT

GGGGGAGGCA GTTTCCGGAC CCCCATCCAA GAGGAGCAGG

CCGACGCCCA CTCCACCCTG GCCAAGATC
```

As used herein, the term "CD3 zeta signaling domain" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD3 zeta signaling domain sequence as shown herein. The example sequences of the CD3 zeta signaling domain are provided in U.S. application Ser. No. 13/826,258 (published as US 2013/0266551). The sequence associated with the CD3 zeta signaling domain is listed as follows (SEQ ID NO: 41):

```
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR,
``` and equivalents thereof.

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface.

As used herein, the term "NK cell," also known as natural killer cell, refers to a type of lymphocyte that originates in the bone marrow and play a critical role in the innate immune system. NK cells provide rapid immune responses against viral-infected cells, tumor cells or other stressed cell, even in the absence of antibodies and major histocompatibility complex on the cell surfaces.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As used herein, the term signal peptide or signal polypeptide intends an amino acid sequence usually present at the N-terminal end of newly synthesized secretory or membrane polypeptides or proteins. It acts to direct the polypeptide across or into a cell membrane and is then subsequently removed. Examples of such are well known in the art. Non-limiting examples are those described in U.S. Pat. Nos. 8,853,381 and 5,958,736.

As used herein, the term "vector" refers to a nucleic acid construct deigned for transfer between different hosts, including but not limited to a plasmid, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector.

As used herein, the term "isolated cell" generally refers to a cell that is substantially separated from other cells of a tissue. The term includes prokaryotic and eukaryotic cells.

"Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses.

The term "transduce" or "transduction" as it is applied to the production of chimeric antigen receptor cells refers to the process whereby a foreign nucleotide sequence is introduced into a cell. In some embodiments, this transduction is done via a vector.

As used herein, the term "autologous," in reference to cells refers to cells that are isolated and infused back into the same subject (recipient or host). "Allogeneic" refers to non-autologous cells.

An "effective amount" or "efficacious amount" refers to the amount of an agent (e.g., a HLA-DR CAR cell), or combined amounts of two or more agents, that, when administered for the treatment of a mammal or other subject, is sufficient to effect such treatment for the disease. The "effective amount" will vary depending on the agent(s), the disease and its severity and the age, weight, etc., of the subject to be treated.

A "solid tumor" is an abnormal mass of tissue that usually does not contain cysts or liquid areas. Solid tumors can be benign or malignant. Different types of solid tumors are named for the type of cells that form them. Examples of solid tumors include sarcomas, carcinomas, and lymphomas.

The term "B cell lymphoma or leukemia" refers to a type of cancer that forms in issues of the lymphatic system or bone marrow, and has undergone a malignant transformation that makes the cells within the cancer pathological to the host organism with the ability to invade or spread to other parts of the body.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions disclosed herein. Aspects defined by each of these transition terms are within the scope of the present disclosure.

As used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}P$, $^{35}S$ or $^{125}I$.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical," percent "identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences disclosed herein.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at www.cancer.gov, last visited on May 1, 2008. Typically, a patient is given a subsequent chemotherapy regimen because the patient did not show a positive clinical or sub-clinical response to the first line therapy or the first line therapy has stopped.

In one aspect, the term "equivalent" or "biological equivalent" of an antibody means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

It is to be inferred without explicit recitation and unless otherwise intended, that when the present disclosure relates to a polypeptide, protein, polynucleotide, antibody or fragment thereof, an equivalent or a biologically equivalent of such is intended within the scope of this disclosure. As used herein, the term "biological equivalent thereof" is intended to be synonymous with "equivalent thereof" when referring to a reference protein, antibody or fragment thereof, polypeptide or nucleic acid, intends those having minimal homology while still maintaining desired structure or functionality. Unless specifically recited herein, it is contemplated that any of the above also includes equivalents thereof. For example, an equivalent intends at least about 70% homology or identity, or at least 80% homology or identity and alternatively, or at least about 85%, or alternatively at least about 90%, or alternatively at least about 95%, or alternatively at least 98% percent homology or identity and exhibits substantially equivalent biological activity to the reference protein, polypeptide, antibody or fragment thereof or nucleic acid. Alternatively, when referring to polynucleotides, an equivalent thereof is a polynucleotide that hybridizes under stringent conditions to the reference polynucleotide or its complement. Alternatively, when referring to polypeptides or proteins, an equivalent thereof is a expressed polypeptide or protein from a polynucleotide that hybridizes under stringent conditions to the polynucleotide or its complement that encodes the reference polypeptide or protein.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A "normal cell corresponding to the tumor tissue type" refers to a normal cell from a same tissue type as the tumor tissue. A non-limiting example is a normal lung cell from a patient having lung tumor, or a normal colon cell from a patient having colon tumor.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "specific binding" means the contact between an antibody and an antigen with a binding affinity of at least $10^{-6}$ M. In certain aspects, antibodies bind with affinities of at least about $10^{-7}$M, and preferably $10^{-8}$ M, $10^{-9}$ M, $10^{-10}$ M, $10^{-11}$ M, or $10^{-12}$ M.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. When the disease is cancer, the following clinical end points are non-limiting examples of treatment: reduction in tumor burden, slowing of tumor growth, longer overall survival, longer time to tumor progression, inhibition of metastasis or a reduction in metastasis of the tumor.

As used herein, the term "overexpress" with respect to a cell, a tissue, or an organ expresses a protein to an amount that is greater than the amount that is produced in a control cell, a control issue, or an organ. A protein that is overexpressed may be endogenous to the host cell or exogenous to the host cell.

As used herein the term "linker sequence" relates to any amino acid sequence comprising from 1 to 10, or alternatively, 8 amino acids, or alternatively 6 amino acids, or alternatively 5 amino acids that may be repeated from 1 to 10, or alternatively to about 8, or alternatively to about 6, or alternatively about 5, or 4 or alternatively 3, or alternatively 2 times. For example, the linker may comprise up to 15 amino acid residues consisting of a pentapeptide repeated three times. Non-limiting examples of linker sequences are known in the art, e.g., GGGGSGGGGSGGGG (and equivalents thereof) (SEQ ID NO: 49); the tripeptide EFM; or Glu-Phe-Gly-Ala-Gly-Leu-Val-Leu-Gly-Gly-Gln-Phe-Met (SEQ ID NO: 50), and equivalents of each thereof. In one aspect, the linker sequence is a (Glycine4Serine)3 flexible polypeptide linker (SEQ ID NO: 51) comprising three copies of gly-gly-gly-gly-ser (SEQ ID NO: 52), and equivalents thereof.

As used herein, the term "enhancer", as used herein, denotes sequence elements that augment, improve or ameliorate transcription of a nucleic acid sequence irrespective of its location and orientation in relation to the nucleic acid sequence to be expressed. An enhancer may enhance transcription from a single promoter or simultaneously from more than one promoter. As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a wild-type enhancer sequence are also within the above definition.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors.

As used herein, the term "WPRE" or "Woodchuck Hepatitis Virus (WHP) Post-transcriptional Regulatory Element" refers to a specific nucleotide fragment associated with this name and any other molecules that have analogous biological function that share at least 70%, or alternatively at least 80% amino acid sequence identity, preferably 90% sequence identity, more preferably at least 95% sequence identity with the WPRE sequence as shown herein. For example, WPRE refers to a region similar to the human hepatitis B virus posttranscriptional regulatory element (HBVPRE) present in the Woodchuck hepatitis virus genomic sequence (GenBank Accession No. J04514), and that the 592 nucleotides from position 1093 to 1684 of this genomic sequence correspond to the post-transcriptional regulatory region (Donello, J. E. et al. (1998) Journal of Virology 72:5085-5092). The analysis using retroviral vectors revealed that WPRE inserted into the 3'-terminal untranslated region of a gene of interest increases the amount of protein produced by 5 to 8 folds. It has also been reported that the introduction of WPRE suppresses mRNA degradation (Zufferey, R. et al. (1999) Journal of Virology 73:2886-2892). In a broad sense, elements such as WPRE that increase the efficiency of amino acid translation by stabilizing mRNAs are also thought to be enhancers.

LIST OF ABBREVIATIONS

CAR: chimeric antigen receptor
HLA: histocompatibility lymphocyte antigen
Ip: intraperitoneal
IRES: internal ribosomal entry site
MFI: mean fluorescence intensity
MOI: multiplicity of infection
PBMC: peripheral blood mononuclear cells
PBS: phosphate buffered saline
scFv: single chain variable fragment
WPRE: woodchuck hepatitis virus post-transcriptional regulatory element

MODES FOR CARRYING OUT THE DISCLOSURE

Due to the unprecedented results being recently obtained in B-cell lymphomas and leukemia's using autologous treatment with genetically engineered chimeric antigen receptor (CAR) T-cells (Maude, S. L. et al. (2014) New Engl. J. Med. 371:1507-1517; Porter, D. L. et al. (2011) New Engl. J. Med. 365:725-733), a number of laboratories have begun to apply this approach to solid tumors including ovarian cancer, prostate cancer, and pancreatic tumors. CAR modified T-cells combine the HLA-independent targeting specificity of a monoclonal antibody with the cytolytic activity, proliferation, and homing properties of activated T-cells, but do not respond to checkpoint suppression. Because of their ability to kill antigen expressing targets directly, CAR T-cells are highly toxic to any antigen positive cells or tissues making it a requirement to construct CARs with highly tumor specific antibodies. To date, CAR modified T-cells to human solid tumors have been constructed against the α-folate receptor, mesothelin, and MUC-CD, PSMA, and other targets but most have some off-target expression of antigen in normal tissues. These constructs have not shown the same exceptional results in patients emphasizing the need for additional studies to identify new targets and methods of CAR T-cell construction that can be used against solid tumors.

Thus, this disclosure provides antibodies specific to HLA-DR and methods and compositions relating to the use and production thereof. In addition, this disclosure provides as a chimeric antigen receptor (CAR) comprising an antigen binding domain specific to HLA-DR, that in some aspects, is the antigen binding domain of Lym-1 and Lym-2 antibodies and methods and compositions relating to the use and production thereof.
Antibodies and Uses Thereof
I. Compositions The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e., the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In one aspect, the present disclosure provides an isolated antibody comprising a heavy chain (HC) immunoglobulin variable domain sequence and a light chain (LC) immunoglobulin variable domain sequence, wherein the heavy chain and light chain immunoglobulin variable domain sequences form an antigen binding site that binds to an epitope of human HLA-DR.

In some embodiments, the heavy chain variable region comprises a CDRH1 sequence comprising, or alternatively consisting essentially of, or yet further consisting of, an amino acid sequence beginning with any one of the following sequences (i) GFSLTSYG (SEQ ID NO: 1), (ii) GFTF-SNYW (SEQ ID NO: 2), or equivalents of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the heavy chain variable region comprises a CDRH2 sequence comprising, or alternatively consisting essentially of, or yet further consisting of, an amino acid sequence beginning with any one of the following sequences: (i) IWSDGST (SEQ ID NO: 3), (ii) IRFK-SHNYAT (SEQ ID NO: 4), or equivalents of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the heavy chain variable region comprises a CDRH3 sequence comprising, or alternatively consisting essentially of, or yet further consisting of, an amino acid sequence beginning with any one of the following sequences: (i) ASHYGSTLAFAS (SEQ ID NO: 5), (ii) TRRIGNSDYDWWYFDV (SEQ ID NO: 6), or equivalents of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the heavy chain variable region comprises, or alternatively consists essentially of, or yet further consists of, the polypeptide encoded by the below noted polynucleotide sequence:

(SEQ ID NO: 7)
CAGGTGCAGCTGAAGGAGTCAGGACCTGGCCTGGTGGCGCCCTCACAGAG

CCTGTCCATCACATGCACCATCTCAGGGTTCTCATTAACCAGCTATGGTG

TACACTGGGTTCGCCAGCCTCCAGGAAAGGGTCTGGAGTGGCTGGTAGTG

ATATGGAGTGATGGAAGCACAACCTATAATTCAGCTCTCAAATCCAGACT

GAGCATCAGCAAGGACAACTCCAAGAGCCAAGTTTTCTTAAAAATGAACA

GTCTCCAAACTGATGACACAGCCATATACTACTGTGCCAGTCACTACGGT

AGTACCCTTGCCTTTGCTTCCTGGGGCCACGGGACTCTGGTCACTGTCTC

TGCA, or an antigen binding fragment thereof or an equivalent of each thereof.

In some embodiments, the heavy chain variable region comprises, or alternatively consists essentially of, or yet further consists of, the amino acid sequence:

(SEQ ID NO: 8)
QLKESGPGLVAPSQSLSITCTISGFSLTSYGVHWVRQPPGKGLEWLVVIW

SDGSTTYNSALKSRLSISKDNSKSQVFLKMNSLQTDDTAIYYCASHYGST

LAFASWGHGTLVTVSA, or an antigen binding fragment thereof or an equivalent of each thereof.

In some embodiments, the heavy chain variable region comprises, or alternatively consists essentially of, or yet further consists of, the polypeptide encoded by the below noted polynucleotide sequence:

(SEQ ID NO: 9)
GAAGTGCAGCTTGAGGAGTCTGGAGGAGGCTTGGTGCAACCTGGAGGCTC

CATGAAACTCTCCTGTGTTGCCTCTGGATTCACTTTCAGTAACTATTGGA

TGAACTGGGTCCGCCAGTCTCCAGAGAAGGGGCTTGAGTGGGTTGCTGAA

ATTAGATTTAAATCTCATAATTATGCAACACATTTTGCGGAGTCTGTGAA

AGGGAGGTTCACCATCTCAAGAGATGATTCCAAAAGTAGTGTCTACCTGC

AAATGAACAACTTAAGAGCTGAAGACACTGGCATTTATTACTGTACCAGG

AGGATAGGAAACTCTGATTACGACTGGTGGTACTTCGATGTCTGGGGCGC

AGGGACCTCAGTCACCGTCTCCTCAGCTAGC, or an antigen binding fragment thereof or an equivalent of each thereof.

In some embodiments, the heavy chain variable region comprises, or alternatively consists essentially of, or yet further consists of, the amino acid sequence:

(SEQ ID NO: 10)
EVQLEESGGGLVQPGGSMKLSCVASGFTFSNYWMNWVRQSPEKGLEWVAE

IRFKSHNYATHFAESVKGRFTISRDDSKSSVYLQMNNLRAEDTGIYYCTR

RIGNSDYDWWYFDVWGAGTSVTVSSAS, or an antigen binding fragment thereof or an equivalent of each thereof.

In some embodiments, the light chain variable region comprises a CDRL1 sequence comprising, or alternatively consisting essentially of, or yet further consisting of, an amino acid sequence beginning with any one of the following sequences (i) VNIYSY (SEQ ID NO: 11), (ii) QNVGNN (SEQ ID NO: 12), or equivalents of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the light chain variable region comprises a CDRL2 sequence comprising, or alternatively consisting essentially of, or yet further consisting of, an amino acid sequence beginning with (i) NAK (SEQ ID NO: 13), (ii) SAS (SEQ ID NO: 14), or equivalents of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In other embodiments, the light chain variable region comprises a CDRL3 sequence comprising, or alternatively consisting essentially of, or yet further consisting of, an amino acid sequence beginning (i) QHHYGTFT (SEQ ID NO: 15), (ii) QQYNTYPFT (SEQ ID NO: 16), or equivalents of each thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the light chain variable region comprises, or alternatively consists essentially of, or yet further consists of, the polypeptide encoded by the polynucleotide sequence:

(SEQ ID NO: 17)
GACATCCAGATGACTCAGTCTCCAGCCTCCCTATCTGCATCTGTGGGAGA

AACTGTCACCATCATATGTCGAGCAAGTGTGAATATTTACAGTTATTTAG

CATGGTATCAGCAGAAACAGGGAAAATCTCCTCAGCTCCTGGTCTATAAT

GCCAAAATCTTAGCAGAAGGTGTGCCATCAAGGTTCAGTGGCAGTGGATC

AGGCACACAGTTTTCTCTGAAGATCAACAGCCTGCAGCCTGAAGATTTTG

GGAGTTATTACTGTCAACATCATTATGGTACATTCACGTTCGGCTCGGGG

ACAAAGTTGGAAATAAAA, or an antigen binding fragment thereof or an equivalent of each thereof.

In some embodiments, the light chain variable region comprises, or alternatively consists essentially of, or yet further consists of, the amino acid sequence:

(SEQ ID NO: 18)
DIQMTQSPASLSASVGETVTIICRASVNIYSYLAWYQQKQGKSPQLLVYN

AKILAEGVPSRFSGSGSGTQFSLKINSLQPEDFGSYYCQHHYGTFTFGSG

TKLEIK, or an antigen binding fragment thereof or an equivalent of each thereof.

In some embodiments, the light chain variable region comprises, or alternatively consists essentially of, or yet further consists of, the polypeptide encoded by the polynucleotide sequence:

(SEQ ID NO: 19)
GACATTGTGATGACCCAGTCTCACAAATTCATGTCCACATCAGTAGGAGA

CAGGGTCAGCGTCACCTGCAAGGCCAGTCAGAATGTGGGTAATAATGTAG

CCTGGTATCAACAGAAACCAGGGCAATCTCCTAAAGTACTGATTTACTCG

GCATCCTACCGGTACAGTGGAGTCCCTGATCGCTTCACAGGCAGTGGATC

TGGGACAGATTTCACTCTCACCATCAGTAATGTGCAGTCTGAAGACTTGG

CAGAGTATTTCTGTCAGCAATATAACACCTATCCATTCACGTTCGGCTCG

GGGACAAAGTTGGAAATAAAA, or an antigen binding fragment thereof or an equivalent of each thereof.

In some embodiments, the light chain variable region comprises, or alternatively consists essentially of, or yet further consists of, the amino acid sequence:

(SEQ ID NO: 20)
DIVMTQSHKFMSTSVGDRVSVTCKASQNVGNNVAWYQQKPGQSPKVLIYS

ASYRYSGVPDRFTGSGSGTDFTLTISNVQSEDLAEYFCQQYNTYPFTFGS

GTKLEIK, or an antigen binding fragment thereof or an equivalent of each thereof.

In another aspect of the present technology, the isolated antibody includes one or more of the following characteristics:

(a) the light chain immunoglobulin variable domain sequence comprises one or more CDRs that are at least 85% identical to a CDR of a light chain variable domain of any of the disclosed light chain sequences;

(b) the heavy chain immunoglobulin variable domain sequence comprises one or more CDRs that are at least 85% identical to a CDR of a heavy chain variable domain of any of the disclosed heavy chain sequences;

(c) the light chain immunoglobulin variable domain sequence is at least 85% identical to a light chain variable domain of any of the disclosed light chain sequences;

(d) the HC immunoglobulin variable domain sequence is at least 85% identical to a heavy chain variable domain of any of the disclosed light chain sequences; and (e) the antibody binds an epitope that overlaps with an epitope bound by any of the disclosed sequences.

Exemplary antibodies comprising the disclosed CDR sequences and heavy and light chain variable sequences are disclosed in Table 1 and Table 2, respectively.

TABLE 1

| ANTI-BODY | CDRH1 | CDRH2 | CDRH3 | CDRL1 | CDRL2 | CDRL3 |
|---|---|---|---|---|---|---|
| Lym-1 | SEQ ID NO: 1 | SEQ ID NO: 3 | SEQ ID NO: 5 | SEQ ID NO: 11 | SEQ ID NO: 13 | SEQ ID NO: 15 |
| Lym-2 | SEQ ID NO: 2 | SEQ ID NO: 4 | SEQ ID: NO 6 | SEQ ID NO: 12 | SEQ ID NO: 14 | SEQ ID NO: 16 |

TABLE 2

| ANTIBODY | Heavy Chain Variable Region | Light Chain Variable Region |
|---|---|---|
| Lym-1 | SEQ ID NO: 7 and 8 | SEQ ID NO: 17 and 18 |
| Lym-2 | SEQ ID NO: 9 and 10 | SEQ ID NO: 19 and 20 |

In one aspect, the present disclosure provides an isolated antibody that is at least 85% identical to an antibody selected from the group consisting of Lym-1 and Lym-2.

In one aspect, the present disclosure provides an isolated antibody comprising the CDRs of Lym-1. In one aspect, the present disclosure provides an isolated antibody that is at least 85% identical to Lym-1.

In one aspect, the present disclosure provides an isolated antibody comprising the CDRs of Lym-2. In one aspect, the present disclosure provides an isolated antibody that is at least 85% identical to Lym-2.

In some aspects of the antibodies provided herein, the HC variable domain sequence comprises, or consists essentially of, or yet further consists of, a variable domain sequence of Lym-1 and the LC variable domain sequence comprises, or consists essentially of, or yet further consists of a variable domain sequence of Lym-1.

In some aspects of the antibodies provided herein, the HC variable domain sequence comprises, or consists essentially of, or yet further consists of, a variable domain sequence of Lym-2 and the LC variable domain sequence comprises, or consists essentially of, or yet further consists of a variable domain sequence of Lym-2.

In some of the aspects of the antibodies provided herein, the antibody binds human HLA-DR with a dissociation constant ($K_D$) of less than $10^{-4}$M, $10^{-5}$M, $10^{-6}$M, $10^{-7}$M, $10^{-8}$M, $10^{-9}$M, $10^{-10}$ M, $10^{-11}$ M, or $10^{-12}$M. In some of the aspects of the antibodies provided herein, the antigen binding site specifically binds to human HLA-DR.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab)'2, Fab', scF$_v$, and F$_v$.

In some of the aspects of the antibodies provided herein, the antibody comprises an Fc domain. In some of the aspects of the antibodies provided herein, the antibody is a rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.

2) Amino acids with acidic side chains: aspartic acid, glutamic acid

3) Amino acids with uncharged polar side chains: asparagine, glutamine, serine, threonine, tyrosine.

4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind HLA-DR with similar specificity and sensitivity profiles as the disclosed antibodies. This may be tested by way of the binding assays known to skill in the art and briefly described herein.

The constant regions of antibodies can also be varied. For example, antibodies are provided with Fc regions of any isotype: IgA (IgA1, IgA2), IgD, IgE, IgG (IgG1, IgG2, IgG3, IgG4) or IgM. Non-limiting examples of constant region sequences include:

```
Human IgD constant region, Uniprot: P01880
                                    (SEQ ID NO: 21)
APTKAPDVFPIISGCRHPKDNSPVVLACLITGYHPTSVTVTWYMGTQSQP

QRTFPEIQRRDSYYMTSSQLSTPLQQWRQGEYKCVVQHTASKSKKEIFRW

PESPKAQASSVPTAQPQAEGSLAKATTAPATTRNTGRGGEEKKKEKEKEE

QEERETKTPECPSHTQPLGVYLLTPAVQDLWLRDKATFTCFVVGSDLKDA

HLTWEVAGKVPTGGVEEGLLERHSNGSQSQHSRLTLPRSLWNAGTSVTCT

LNHPSLPPQRLMALREPAAQAPVKLSLNLLASSDPPEAASWLLCEVSGFS

PPNILLMWLEDQREVNTSGFAPARPPPQPGSTTFWAWSVLRVPAPPSPQP

ATYTCVVSHEDSRTLLNASRSLEVSYVTDHGPMK,
``` and equivalents thereof.

```
Human IgG1 constant region, Uniprot: P01857
                                    (SEQ ID NO: 22)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK,
``` and equivalents thereof.

```
Human IgG2 constant region, Uniprot: P01859
                                    (SEQ ID NO: 23)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDISVEWESNGQPENNYKTTPPMLDSDGSFFLYSKLTVDKSRWQQGN

VFSCSVMHEALHNHYTQKSLSLSPGK,
``` and equivalents thereof.

```
Human IgG3 constant region, Uniprot: P01860
                                    (SEQ ID NO: 24)
ASTKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVEL

KTPLGDTTHTCPRCPEPKSCDTPPPCPRCPEPKSCDTPPPCPRCPEPKSC

DTPPPCPRCPAPELLGGPSVFLFPPKPKDTLMISRTPEVTCVVVDVSHED

PEVQFKWYVDGVEVHNAKTKPREEQYNSTFRVVSVLTVLHQDWLNGKEYK

CKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQG

NIFSCSVMHEALHNRFTQKSLSLSPGK,
``` and equivalents thereof.

```
Human IgM constant region, Uniprot: P01871
                                    (SEQ ID NO: 25)
GSASAPTLFPLVSCENSPSDTSSVAVGCLAQDFLPDSITLSWKYKNNSDI

SSTRGFPSVLRGGKYAATSQVLLPSKDVMQGTDEHVVCKVQHPNGNKEKN

VPLPVIAELPPKVSVFVPPRDGFFGNPRKSKLICQATGFSPRQIQVSWLR

EGKQVGSGVTTDQVQAEAKESGPTTYKVTSTLTIKESDWLGQSMFTCRVD

HRGLTFQQNASSMCVPDQDTAIRVFAIPPSFASIFLTKSTKLTCLVTDLT

TYDSVTISWTRQNGEAVKTHTNISESHPNATFSAVGEASICEDDWNSGER

FTCTVTHTDLPSPLKQTISRPKGVALHRPDVYLLPPAREQLNLRESATIT

CLVTGFSPADVFVQWMQRGQPLSPEKYVTSAPMPEPQAPGRYFAHSILTV

SEEEWNTGETYTCVAHEALPNRVTERTVDKSTGKPTLYNVSLVMSDTAGT

CY,
``` and equivalents thereof.

```
Human IgG4 constant region, Uniprot: P01861
                                    (SEQ ID NO: 26)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GEYPSDIAVEWESNGQPENNYKTTPPVLDSDGSFFLYSRLTVDKSRWQEG

NVFSCSVMHEALHNHYTQKSLSLSLGK,
``` and equivalents thereof.

Human IgA1 constant region, Uniprot: P01876
(SEQ ID NO: 27)
ASPTSPKVFPLSLCSTQPDGNVVIACLVQGFFPQEPLSVTWSESGQGVTA

RNFPPSQDASGDLYTTSSQLTLPATQCLAGKSVTCHVKHYTNPSQDVTVP

CPVPSTPPTPSPSTPPTPSPSCCHPRLSLHRPALEDLLLGSEANLTCTLT

GLRDASGVTFTWTPSSGKSAVQGPPERDLCGCYSVSSVLPGCAEPWNHGK

TFTCTAAYPESKTPLTATLSKSGNTFRPEVHLLPPPSEELALNELVTLTC

LARGFSPKDVLVRWLQGSQELPREKYLTWASRQEPSQGTTTFAVTSILRV

AAEDWKKGDTFSCMVGHEALPLAFTQKTIDRLAGKPTHVNVSVVMAEVDG

TCY, and equivalents thereof.

Human IgA2 constant region, Uniprot: P01877
(SEQ ID NO: 28)
ASPTSPKVFPLSLDSTPQDGNVVVACLVQGFFPQEPLSVTWSESGQNVTA

RNFPPSQDASGDLYTTSSQLTLPATQCPDGKSVTCHVKHYTNPSQDVTVP

CPVPPPPPCCHPRLSLHRPALEDLLLGSEANLTCTLTGLRDASGATFTWT

PSSGKSAVQGPPERDLCGCYSVSSVLPGCAQPWNHGETFTCTAAHPELKT

PLTANITKSGNTFRPEVHLLPPPSEELALNELVTLTCLARGFSPKDVLVR

WLQGSQELPREKYLTWASRQEPSQGTTTFAVTSILRVAAEDWKKGDTFSC

MVGHEALPLAFTQKTIDRMAGKPTHVNVSVVMAEVDGTCY, and equivalents thereof.

Human Ig kappa constant region, Uniprot: P01834
(SEQ ID NO: 29)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC, and equivalents thereof.

In some aspects, the antibodies comprise a heavy chain constant region that is at least 80% identical to any one of SEQ ID NOs: 7 to 10.

In some aspects, the antibodies comprise a light chain constant region that is at least 80% identical to any one of SEQ ID NOs: 17 to 20.

In some aspects of the antibodies provided herein, the antibody binds to the epitope bound by Lym-1 and Lym-2 antibodies.

In some aspects of the antibodies provided herein, the HLA-DR-specific antibody competes for binding to human HLA-DR with Lym-1 and Lym-2.

In some aspects of the antibodies provided herein, the antibody contains structural modifications to facilitate rapid binding and cell uptake and/or slow release. In some aspects, the HLA-DR antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

The antibodies, fragments, and equivalents thereof can be combined with a carrier, e.g., a pharmaceutically acceptable carrier or other agents to provide a formulation for use and/or storage.

Further provided is an isolated polypeptide comprising, or alternatively consisting essentially of, or yet further consisting of, the amino acid sequence of HLA-DR or a fragment thereof, that are useful to generate antibodies that bind to HLA-DR, as well as isolated polynucleotides that encode them. In one aspect, the isolated polypeptides or polynucleotides further comprise a label and/or contiguous polypeptide sequences (e.g., keyhole limpet haemocyanin (KLH) carrier protein) or in the case of polynucleotides, polynucleotides encoding the sequence, operatively coupled to polypeptide or polynucleotide. The polypeptides or polynucleotides can be combined with various carriers, e.g., phosphate buffered saline. Further provided are host cells, e.g., prokaryotic or eukaryotic cells, e.g., bacteria, yeast, mammalian (rat, simian, hamster, or human), comprising the isolated polypeptides or polynucleotides. The host cells can be combined with a carrier.

II. Processes for Preparing Compositions

Antibodies, their manufacture and uses are well known and disclosed in, for example, Harlow, E. and Lane, D. (1999) *Antibodies: A Laboratory Manual*, Cold Spring Harbor Laboratory Press, Cold Spring Harbor, N.Y. The antibodies may be generated using standard methods known in the art. Examples of antibodies include (but are not limited to) monoclonal, single chain, and functional fragments of antibodies. Methods for generating such antibodies are known in the art; see, e.g. Collarini et al. (2009) J. Immunol. 183(10):6338-6345.

Antibodies may be produced in a range of hosts, for example goats, rabbits, rats, mice, humans, and others. They may be immunized by injection with a target antigen or a fragment or oligopeptide thereof which has immunogenic properties, such as a C-terminal fragment of HLA-DR or an isolated polypeptide. Depending on the host species, various adjuvants may be added and used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful. This this disclosure also provides the isolated polypeptide and an adjuvant.

In certain aspects, the antibodies of the present disclosure are polyclonal, i.e., a mixture of plural types of anti-HLA-DR antibodies having different amino acid sequences. In one aspect, the polyclonal antibody comprises a mixture of plural types of anti-HLA-DR antibodies having different CDRs. As such, a mixture of cells which produce different antibodies is cultured, and an antibody purified from the resulting culture can be used (see International Patent Application Publication No. WO 2004/061104).

Monoclonal Antibody Production.

Monoclonal antibodies to HLA-DR may be prepared using any technique which provides for the production of antibody molecules by continuous cell lines in culture. Such techniques include, but are not limited to, the hybridoma technique (see, e.g., Kohler, G. et al. (1975) Nature 256: 495-497); the trioma technique; the human B-cell hybridoma technique (see, e.g., Kozbor, D. et al. (1983) Immunol. Today 4:72) and the EBV hybridoma technique to produce human monoclonal antibodies (see, e.g., Cole et al. (1985) in *Monoclonal Antibodies and Cancer Therapy*, Alan R. Liss, Inc., 77-96). Human monoclonal antibodies can be utilized in the practice of the present technology and can be produced by using human hybridomas (see, e.g., Cote, R. J. et al. (1983) Proc. Natl. Acad. Sci. U.S.A. 80:2026-2030) or by transforming human B-cells with Epstein Barr Virus in vitro (see, e.g., Cole et al. (1985) in *Monoclonal Antibodies and Cancer Therapy*, Alan R. Liss, Inc., 77-96). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the HLA-DR polypeptide. Alternatively, hybridomas expressing anti-HLA-DR monoclonal antibodies can be prepared by immunizing a subject, e.g., with an isolated polypeptide comprising, or alternatively consisting essentially of, or yet further consisting of, the amino acid sequence of HLA-DR or a fragment thereof, and then isolating hybridomas from the subject's spleen using routine methods. See, e.g., Galfre, G. et al. (1981) Methods Enzymol. 73:3-46. Screening the hybridomas using standard methods will produce monoclonal antibodies of varying specificity (i.e., for different epitopes) and affinity. A selected monoclonal antibody with the desired properties, e.g., HLA-DR binding, can be (i) used as expressed by the hybridoma, (ii) bound to a molecule such as polyethylene glycol (PEG) to alter its properties, or (iii) a cDNA encoding the monoclonal antibody can be isolated, sequenced and manipulated in various ways. In one aspect, the anti-HLA-DR monoclonal antibody is produced by a hybridoma which includes a B cell obtained from a transgenic non-human animal, e.g., a transgenic mouse, having a genome comprising a human heavy chain transgene and a light chain transgene fused to an immortalized cell. Hybridoma techniques include those known in the art and taught in Harlow et al. (1988) *Antibodies: A Laboratory Manual* Cold Spring Harbor Laboratory, Cold Spring Harbor, N.Y., 349; Hammerling et al. (1981) *Monoclonal Antibodies And T-Cell* Hybridomas, 563-681.

Phage Display Technique.

As noted above, the antibodies of the present disclosure can be produced through the application of recombinant DNA and phage display technology. For example, anti-HLA-DR antibodies, can be prepared using various phage display methods known in the art. In phage display methods, functional antibody domains are displayed on the surface of a phage particle which carries polynucleotide sequences encoding them. Phage with a desired binding property is selected from a repertoire or combinatorial antibody library (e.g., human or murine) by selecting directly with an antigen, typically an antigen bound or captured to a solid surface or bead. Phage used in these methods are typically filamentous phage including fd and M13 with Fab, $F_v$ or disulfide stabilized $F_v$ antibody domains are recombinantly fused to either the phage gene III or gene VIII protein. In addition, methods can be adapted for the construction of Fab expression libraries (see, e.g., Huse, W. D. et al. (1989) Science 246:1275-1281) to allow rapid and effective identification of monoclonal Fab fragments with the desired specificity for a HLA-DR polypeptide, e.g., a polypeptide or derivatives, fragments, analogs or homologs thereof. Other examples of phage display methods that can be used to make the isolated antibodies of the present disclosure include those disclosed in Huston, J. S. et al. (1988) Proc. Natl. Acad. Sci. U.S.A. 85:5879-5883; Chaudhary, V. K. et al. (1990) Proc. Natl. Acad. Sci. U.S.A., 87:1066-1070; Brinkman et al., J. Immunol. Methods 182: 41-50 (1995); Ames, R. S. et al. (1995) J. Immunol. Methods 184:177-186; Kettleborough et al., Eur. J. Immunol. 24: 952-958 (1994); Persic, L. et al. (1997) Gene 187:9-18; Burton, D. R. et al. (1994) Advances in Immunology 57:191-280; International Patent Application No. PCT/GB91/01134; International Patent Application Publication Nos. WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727 and 5,733,743.

Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in International Patent Application Publication No. WO 92/22324; Mullinax, R. L. et al. (1992) BioTechniques 12:864-869; Sawai, H. et al. (1995) AJRI 34:26-34; and Better, M. et al. (1988) Science 240:1041-1043.

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g., Barbas III et al., *Phage Display, A Laboratory Manual* (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Alternate Methods of Antibody Production.

Antibodies may also be produced by inducing in vivo production in the lymphocyte population or by screening recombinant immunoglobulin libraries or panels of highly specific binding reagents (Orlandi, R. et al. (1989) Proc. Natl. Acad. Sci. USA 86:3833-3837; Winter, G. et al. (1991) Nature 349:293-299).

Alternatively, techniques for the production of single chain antibodies may be used. Single chain antibodies (scF$_v$s) comprise a heavy chain variable region and a light chain variable region connected with a linker peptide (typically around 5 to 25 amino acids in length). In the scF$_v$, the variable regions of the heavy chain and the light chain may be derived from the same antibody or different antibodies. scF$_v$s may be synthesized using recombinant techniques, for example by expression of a vector encoding the scF$_v$ in a host organism such as *E. coli*. DNA encoding scF$_v$ can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scF$_v$ and a host transformed by the expression vector can be obtained according to conventional methods known in the art.

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse, W. D. et al. (1989) Science 256:1275-1281).

Antibody Modifications.

The antibodies of the present disclosure may be multimerized to increase the affinity for an antigen. The antibody to be multimerized may be one type of antibody or a plurality of antibodies which recognize a plurality of epitopes of the same antigen. As a method of multimerization of the antibody, binding of the IgG CH3 domain to two scF$_v$ molecules, binding to streptavidin, introduction of a helix-turn-helix motif and the like can be exemplified.

The antibody compositions disclosed herein may be in the form of a conjugate formed between any of these antibodies and another agent (immunoconjugate). In one aspect, the antibodies disclosed herein are conjugated to radioactive material. In another aspect, the antibodies disclosed herein can be bound to various types of molecules such as polyethylene glycol (PEG).

Antibody Screening.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HLA-DR, or any fragment or oligopeptide thereof and its specific antibody. A two-site, monoclonal-based immunoassay utilizing monoclonal antibodies specific to two non-interfering HLA-DR epitopes may be used, but a competitive binding assay may also be employed (Maddox, D. E. et al. (1983) J. Exp. Med. 158:1211-1216).

Antibody Purification.

The antibodies disclosed herein can be purified to homogeneity. The separation and purification of the antibodies can be performed by employing conventional protein separation and purification methods.

By way of example only, the antibody can be separated and purified by appropriately selecting and combining use of chromatography columns, filters, ultrafiltration, salt precipitation, dialysis, preparative polyacrylamide gel electrophoresis, isoelectric focusing electrophoresis, and the like. *Strategies for Protein Purification and Characterization: A Laboratory Course Manual*, Marshak, D. R. et al. eds., Cold Spring Harbor Laboratory Press (1996); *Antibodies: A Laboratory Manual*. Ed Harlow and David Lane, Cold Spring Harbor Laboratory (1988).

Examples of chromatography include affinity chromatography, ion exchange chromatography, hydrophobic chromatography, gel filtration chromatography, reverse phase chromatography, and adsorption chromatography. In one aspect, chromatography can be performed by employing liquid chromatography such as HPLC or FPLC.

In one aspect, a Protein A column or a Protein G column may be used in affinity chromatography. Other exemplary columns include a Protein A column, Hyper D, POROS, Sepharose F. F. (Pharmacia) and the like.

Methods of Use

General.

The antibodies disclosed herein are useful in methods known in the art relating to the localization and/or quantitation of a HLA-DR polypeptide (e.g., for use in measuring levels of the HLA-DR polypeptide within appropriate physiological samples, for use in diagnostic methods, for use in imaging the polypeptide, and the like). The antibodies disclosed herein are useful in isolating a HLA-DR polypeptide by standard techniques, such as affinity chromatography or immunoprecipitation. A HLA-DR antibody disclosed herein can facilitate the purification of natural HLA-DR polypeptides from biological samples, e.g., mammalian sera or cells as well as recombinantly-produced HLA-DR polypeptides expressed in a host system. Moreover, HLA-DR antibody can be used to detect a HLA-DR polypeptide (e.g., in plasma, a cellular lysate or cell supernatant) in order to evaluate the abundance and pattern of expression of the polypeptide. The HLA-DR antibodies disclosed herein can be used diagnostically to monitor HLA-DR levels in tissue as part of a clinical testing procedure, e.g., to determine the efficacy of a given treatment regimen. The detection can be facilitated by coupling (i.e., physically linking) the HLA-DR antibodies disclosed herein to a detectable substance.

In another aspect, provided herein is a composition comprising an antibody or antigen binding fragment as disclosed herein bound to a peptide comprising, for example, a human HLA-DR protein or a fragment thereof. In one aspect, the peptide is associated with a cell. For example, the composition may comprise a disaggregated cell sample labeled with an antibody or antibody fragment as disclosed herein, which composition is useful in, for example, affinity chromatography methods for isolating cells or for flow cytometry-based cellular analysis or cell sorting. As another example, the composition may comprise a fixed tissue sample or cell smear labeled with an antibody or antibody fragment as disclosed herein, which composition is useful in, for example, immunohistochemistry or cytology analysis. In another aspect, the antibody or the antibody fragment is bound to a solid support, which is useful in, for example: ELISAs; affinity chromatography or immunoprecipitation methods for isolating HLA-DR proteins or fragments thereof, HLA-DR-positive cells, or complexes containing HLA-DR and other cellular components. In another aspect, the peptide is bound to a solid support. For example, the peptide may be bound to the solid support via a secondary antibody specific for the peptide, which is useful in, for example, sandwich ELISAs. As another example, the peptide may be bound to a chromatography column, which is useful in, for example, isolation or purification of antibodies according to the present technology. In another aspect, the peptide is disposed in a solution, such as a lysis solution or a solution containing a sub-cellular fraction of a fractionated cell, which is useful in, for example, ELISAs and affinity chromatography or immunoprecipitation methods of isolating HLA-DR proteins or fragments thereof or complexes containing HLA-DR and other cellular components. In another aspect, the peptide is associated with a matrix, such as, for example, a gel electrophoresis gel or a matrix commonly used for western blotting (such as membranes made of nitrocellulose or polyvinylidene difluoride), which compositions are useful for electrophoretic and/or immunoblotting techniques, such as Western blotting.

Detection of HLA-DR Polypeptide.

An exemplary method for detecting the level of HLA-DR polypeptides in a biological sample involves obtaining a biological sample from a subject and contacting the biological sample with a HLA-DR binding agent, e.g., an antibody disclosed herein or known in the art that is capable of detecting the HLA-DR polypeptides.

In one aspect, the HLA-DR antibodies Lym-1, or Lym-2, or fragments thereof are detectably labeled. The term "labeled", with regard to the antibody is intended to encompass direct labeling of the antibody by coupling (i.e., physically linking) a detectable substance to the antibody, as well as indirect labeling of the antibody by reactivity with another compound that is directly labeled. Non-limiting examples of indirect labeling include detection of a primary antibody using a fluorescently-labeled secondary antibody and end-labeling of a DNA probe with biotin such that it can be detected with fluorescently-labeled streptavidin.

The detection method of the present disclosure can be used to detect expression levels of HLA-DR polypeptides in a biological sample in vitro as well as in vivo. In vitro techniques for detection of HLA-DR polypeptides include enzyme linked immunosorbent assays (ELISAs), Western blots, flow cytometry, immunoprecipitations, radioimmunoassay, and immunofluorescence (e.g., IHC). Furthermore, in vivo techniques for detection of HLA-DR polypeptides include introducing into a subject a labeled anti-HLA-DR antibody. By way of example only, the antibody can be labeled with a detectable marker, e.g. a radioactive marker whose presence and location in a subject can be detected by standard imaging techniques. In one aspect, the biological sample contains polypeptide molecules from the subject.

Immunoassay and Imaging.

A HLA-DR antibody disclosed herein can be used to assay HLA-DR polypeptide levels in a biological sample (e.g., human plasma) using antibody-based techniques. For example, protein expression in tissues can be studied with classical immunohistochemical (IHC) staining methods. Jalkanen, M. et al. (1985) J. Cell. Biol. 101:976-985; Jalkanen, M. et al. (1987) J. Cell. Biol. 105:3087-3096. Other antibody-based methods useful for detecting protein gene expression include immunoassays, such as the enzyme linked immunosorbent assay (ELISA) and the radioimmunoassay (MA). Suitable antibody assay labels are known in the art and include enzyme labels, such as, glucose oxidase, and radioisotopes or other radioactive agents, such as iodine ($^{125}$I, $^{121}$I, $^{131}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

In addition to assaying HLA-DR polypeptide levels in a biological sample, HLA-DR polypeptide levels can also be detected in vivo by imaging. Labels that can be incorporated with anti-HLA-DR antibodies for in vivo imaging of HLA-DR polypeptide levels include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the HLA-DR antibody by labeling of nutrients for the relevant $scF_v$ clone.

A HLA-DR antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled HLA-DR antibody will then preferentially accumulate at the location of cells which contain the specific target polypeptide. For example, in vivo tumor imaging is described in Burchiel, S. W. et al. (1982) Tumor Imaging: The Radiochemical Detection of Cancer 13.

In some aspects, HLA-DR antibodies containing structural modifications that facilitate rapid binding and cell uptake and/or slow release are useful in in vivo imaging detection methods. In some aspects, the HLA-DR antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

Diagnostic Uses of HLA-DR Antibodies.

The HLA-DR antibody compositions disclosed herein are useful in diagnostic and prognostic methods. As such, the present disclosure provides methods for using the antibodies disclosed herein in the diagnosis of HLA-DR-related medical conditions in a subject. Antibodies disclosed herein may be selected such that they have a high level of epitope binding specificity and high binding affinity to the HLA-DR polypeptide. In general, the higher the binding affinity of an antibody, the more stringent wash conditions can be performed in an immunoassay to remove nonspecifically bound material without removing the target polypeptide. Accordingly, HLA-DR antibodies of the present technology useful in diagnostic assays usually have binding affinities of at least $10^{-6}$, $10^{-7}$, $10^{-8}$, $10^{-9}$, $10^{-10}$, $10^{-11}$, or $10^{-12}$M. In certain aspects, HLA-DR antibodies used as diagnostic reagents have a sufficient kinetic on-rate to reach equilibrium under standard conditions in at least 12 hours, at least 5 hours, at least 1 hour, or at least 30 minutes.

Some methods of the present technology employ polyclonal preparations of anti-HLA-DR antibodies and polyclonal anti-HLA-DR antibody compositions as diagnostic reagents, and other methods employ monoclonal isolates. In methods employing polyclonal human anti-HLA-DR antibodies prepared in accordance with the methods described above, the preparation typically contains an assortment of HLA-DR antibodies, e.g., antibodies, with different epitope specificities to the target polypeptide. The monoclonal anti-HLA-DR antibodies of the present disclosure are useful for detecting a single antigen in the presence or potential presence of closely related antigens.

The HLA-DR antibodies of the present disclosure can be used as diagnostic reagents for any kind of biological sample. In one aspect, the HLA-DR antibodies disclosed herein are useful as diagnostic reagents for human biological samples. HLA-DR antibodies can be used to detect HLA-DR polypeptides in a variety of standard assay formats. Such formats include immunoprecipitation, Western blotting, ELISA, radioimmunoassay, flow cytometry, IHC and immunometric assays. See Harlow & Lane, Antibodies, A Laboratory Manual (Cold Spring Harbor Publications, New York, 1988); U.S. Pat. Nos. 3,791,932; 3,839,153; 3,850, 752; 3,879,262; 4,034,074, 3,791,932; 3,817,837; 3,839, 153; 3,850,752; 3,850,578; 3,853,987; 3,867,517; 3,879, 262; 3,901,654; 3,935,074; 3,984,533; 3,996,345; 4,034,074 and 4,098,876. Biological samples can be obtained from any tissue (including biopsies), cell or body fluid of a subject.

In another aspect, the present disclosure provides methods for determining whether a subject can be effectively treated with CAR T cell or CAR NK cell composition as described herein. The method comprises assaying a cancer or tumor sample isolated from the patient for HLA-DR protein or polypeptide expression using any appropriate method, e.g., immunohistochemistry using an HLA-DR antibody or the polymerase chain reaction (PCR). In one aspect, the expression level of the HLA-DR polypeptide in the biological sample obtained from the subject is determined and compared with HLA-DR expression levels found in a biological sample obtained from a subject or a population of patients free of the disease. Increased expression of the HLA-DR polypeptide, as compared to the expression level of the polypeptide or protein in the patient sample(s) from the patients free of disease indicates that the patient is likely to be responsive to the CAR T cell or CAR NK cell therapy of this disclosure, and lack of elevated expression indicates that the patient is not likely to be responsive to the CAR T cell or CAR NK cell therapy. Non-limiting examples of samples include, e.g., any body fluid including, but not limited to, e.g., sputum, serum, plasma, lymph, cystic fluid, urine, stool, cerebrospinal fluid, ascite fluid or blood and including biopsy samples of body tissue. The samples are also a tumor cell. The test sample used in the above-described method will vary based on the assay format, nature of the detection method and the tissues, cells or extracts used as the sample to be assayed. In a further aspect, an effective amount of the HLA-DR CAR therapy is administered to the subject or patient In a particular aspect, the present disclosure relates to methods for determining if a patient is likely to respond or is not likely to HLA-DR CAR therapy. In specific embodiments, this method comprises contacting a tumor sample isolated from the patient with an effective amount of an HLA-DR binding agent, e.g., an HLA-DR antibody and detecting the presence of any agent or antibody bound to the tumor sample. In further embodiments, the presence of agent or antibody bound to the tumor sample indicates that the patient is likely to respond to the HLA-DR CAR therapy and the absence of antibody bound to the tumor sample indicates that the patient is not likely to respond to the HLA-DR therapy. Non-limiting examples of samples include, e.g., any body fluid including, but not limited to, e.g., sputum, serum, plasma, lymph, cystic fluid, urine, stool, cerebrospinal fluid, ascite fluid or blood and including biopsy samples of body tissue. The samples are also a tumor cell. The test sample used in the above-described method will vary based on the assay format, nature of the detection method and the tissues, cells or extracts used as the sample to be assayed. In some embodiments, the method comprises the additional step of administering an effective amount of the HLA-DR CAR therapy to a patient that is determined likely to respond to the HLA-DR CAR therapy. In some embodiments, the patient a HLA-DR expressing tumor and/or cancer.

There are a number of disease states in which the elevated expression level of HLA-DR polypeptides is known to be indicative of whether a subject with the disease is likely to respond to a particular type of therapy or treatment. Non-limiting examples of such disease states include cancer, e.g., a carcinoma, a sarcoma or a leukemia. Thus, the method of detecting a HLA-DR polypeptide in a biological sample can be used as a method of prognosis, e.g., to evaluate the likelihood that the subject will respond to the therapy or treatment. The level of the HLA-DR polypeptide in a suitable tissue or body fluid sample from the subject is determined and compared with a suitable control, e.g., the level in subjects with the same disease but who have responded favorably to the treatment. Non-limiting examples of samples include, e.g., any body fluid including, but not limited to, e.g., sputum, serum, plasma, lymph, cystic fluid, urine, stool, cerebrospinal fluid, ascite fluid or blood and including biopsy samples of body tissue. The samples are also a tumor cell. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

In one aspect, the present disclosure provides for methods of monitoring the influence of agents (e.g., the CART cell or CAR NK cell compositions of this disclosure, drugs, compounds, or small molecules) on the expression of HLA-DR polypeptides. Such assays can be applied in basic drug screening and in clinical trials. For example, the effectiveness of an agent to decrease HLA-DR polypeptide levels can be monitored in clinical trials of subjects exhibiting elevated expression of HLA-DR, e.g., patients diagnosed with cancer. An agent that affects the expression of HLA-DR polypeptides can be identified by administering the agent and observing a response. In this way, the expression pattern of the HLA-DR polypeptide can serve as a marker, indicative of the physiological response of the subject to the agent. Accordingly, this response state may be determined before, and at various points during, treatment of the subject with the agent. In some embodiments, the method further comprises the additional step of administering an effective amount of the HLA-DR CAR therapy to a patient that is determined to require additional therapy.

Further method aspects of the present disclosure relate to methods for determining if a patient is likely to respond or is not likely to HLA-DR CAR therapy. In specific embodiments, this method comprises contacting a tumor sample isolated from the patient with an effective amount of an HLA-DR antibody and detecting the presence of any antibody bound to the tumor sample. In further embodiments, the presence of antibody bound to the tumor sample indicates that the patient is likely to respond to the HLA-DR CAR therapy and the absence of antibody bound to the tumor sample indicates that the patient is not likely to respond to the HLA-DR therapy. In some embodiments, the method comprises the additional step of administering an effective amount of the HLA-DR CAR therapy to a patient that is determined likely to respond to the HLA-DR CAR therapy. In some embodiments, the patient a HLA-DR expressing tumor and/or cancer.

III. Kits

As set forth herein, the present disclosure provides diagnostic methods for determining the expression level of HLA-DR. In one particular aspect, the present disclosure provides kits for performing these methods as well as instructions for carrying out the methods of the present disclosure such as collecting tissue and/or performing the screen, and/or analyzing the results.

The kit comprises, or alternatively consists essentially of, or yet further consists of, a HLA-DR antibody composition (e.g., monoclonal antibodies) disclosed herein, and instructions for use. The kits are useful for detecting the presence of HLA-DR polypeptides in a biological sample, e.g., any body fluid including, but not limited to, e.g., sputum, serum, plasma, lymph, cystic fluid, urine, stool, cerebrospinal fluid, acitic fluid or blood and including biopsy samples of body tissue. The test samples may also be a tumor cell, a normal cell adjacent to a tumor, a normal cell corresponding to the tumor tissue type, a blood cell, a peripheral blood lymphocyte, or combinations thereof. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

In some aspects, the kit can comprise: one or more HLA-DR antibodies capable of binding and that bind a HLA-DR polypeptide in a biological sample (e.g., an antibody or antigen-binding fragment thereof having the same antigen-binding specificity of HLA-DR antibody Lym-1 or Lym-2); means for determining the amount of the HLA-DR polypeptide in the sample; and means for comparing the amount of the HLA-DR polypeptide in the sample with a standard. One or more of the HLA-DR antibodies may be labeled. The kit components, (e.g., reagents) can be packaged in a suitable container. The kit can further comprise instructions for using the kit to detect the HLA-DR polypeptides. In certain aspects, the kit comprises a first antibody, e.g., attached to a solid support, which binds to a HLA-DR polypeptide; and, optionally; 2) a second, different antibody which binds to either the HLA-DR polypeptide or the first antibody and is conjugated to a detectable label.

The kit can also comprise, e.g., a buffering agent, a preservative or a protein-stabilizing agent. The kit can further comprise components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

IV. Carriers

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation.

Chimeric Antigen Receptors and Uses Thereof

I. Compositions

The present disclosure provides chimeric antigen receptors (CAR) that bind to HLA-DR comprising, or consisting essentially of, a cell activation moiety comprising an extracellular, transmembrane, and intracellular domain. The extracellular domain comprises a target-specific binding element otherwise referred to as the antigen binding domain. The intracellular domain or cytoplasmic domain comprises, a costimulatory signaling region and a zeta chain portion.

The CAR may optionally further comprise a spacer domain of up to 300 amino acids, preferably 10 to 100 amino acids, more preferably 25 to 50 amino acids.

Antigen Binding Domain.

In certain aspects, the present disclosure provides a CAR that comprises, or alternatively consists essentially thereof, or yet consists of an antigen binding domain specific to HLA-DR. In some embodiments, the antigen binding domain comprises, or alternatively consists essentially thereof, or yet consists of the antigen binding domain of an anti-HLA-DR antibody. In further embodiments, the heavy chain variable region and light chain variable region of an anti-HLA-DR antibody comprises, or alternatively consists essentially thereof, or yet consists of the antigen binding domain the anti-HLA-DR antibody.

In some embodiments, the heavy chain variable region of the antibody comprises, or consists essentially thereof, or consists of SEQ ID NOs: 7 to 10 or an equivalent of each thereof and/or comprises one or more CDR regions comprising SEQ ID NOs: 1 to 6 or an equivalent of each thereof. In some embodiments, the light chain variable region of the antibody comprises, or consists essentially thereof, or consists of SEQ ID NOs: 17 to 20 or an equivalent thereof and/or comprises one or more CDR regions comprising SEQ ID NOs: 11 to 16 or an equivalent thereof.

Transmembrane Domain.

The transmembrane domain may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain.

The cytoplasmic domain or intracellular signaling domain of the CAR is responsible for activation of at least one of the traditional effector functions of an immune cell in which a CAR has been placed. The intracellular signaling domain refers to a portion of a protein which transduces the effector function signal and directs the immune cell to perform its specific function. An entire signaling domain or a truncated portion thereof may be used so long as the truncated portion is sufficient to transduce the effector function signal. Cytoplasmic sequences of the TCR and co-receptors as well as derivatives or variants thereof can function as intracellular signaling domains for use in a CAR. Intracellular signaling domains of particular use in this disclosure may be derived from FcR, TCR, CD3, CDS, CD22, CD79a, CD79b, CD66d. Since signals generated through the TCR are alone insufficient for full activation of a T cell, a secondary or co-stimulatory signal may also be required. Thus, the intracellular region of a co-stimulatory signaling molecule, including but not limited CD27, CD28, 4-IBB (CD 137), OX40, CD30, CD40, PD-1, ICOS, lymphocyte function-associated antigen-1 (LFA-1), CD2, CD7, LIGHT, NKG2C, B7-H3, or a ligand that specifically binds with CD83, to may also be included in the cytoplasmic domain of the CAR.

In some embodiments, the cell activation moiety of the chimeric antigen receptor is a T-cell signaling domain comprising, or alternatively consisting essentially of, or yet further consisting of, one or more proteins or fragments thereof selected from the group consisting of CD8 protein, CD28 protein, 4-1BB protein, and CD3-zeta protein.

In specific embodiments, the CAR comprises, or alternatively consists essentially thereof, or yet consists of an antigen binding domain of an anti-HLA-DR antibody, a CD8 α hinge domain, a CD8 α transmembrane domain, a costimulatory signaling region, and a CD3 zeta signaling domain. In further embodiments, the costimulatory signaling region comprises either or both a CD28 costimulatory signaling region and a 4-1BB costimulatory signaling region.

In some embodiments, the CAR can further comprise a detectable marker or purification marker.

In a further aspect, this disclosure provides complex comprising an HLA-DR CAR cell bound to its target cell. In a further aspect, the complex is detectably labeled. Detectable labels are known in the art and briefly described herein.

II. Process for Preparing CARs

Aspects of the present disclosure relate to an isolated cell comprising a HLA-DR CAR and methods of producing such cells. The cell is a prokaryotic or a eukaryotic cell. In one aspect, the cell is a T cell or a NK cell. The eukaryotic cell can be from any preferred species, e.g., an animal cell, a mammalian cell such as a human, a feline or a canine cell.

In specific embodiments, the isolated cell comprises, or alternatively consists essentially of, or yet further consists of an exogenous CAR comprising, or alternatively consisting essentially of, or yet further consisting of, an antigen binding domain of an anti-HLA-DR antibody, a CD8 α hinge domain, a CD8 α transmembrane domain, a CD28 costimulatory signaling region and/or a 4-1BB costimulatory signaling region, and a CD3 zeta signaling domain. In certain embodiments, the isolated cell is a T-cell, e.g., an animal T-cell, a mammalian T-cell, a feline T-cell, a canine T-cell or a human T-cell. In certain embodiments, the isolated cell is an NK-cell, e.g., an animal NK-cell, a mammalian NK-cell, a feline NK-cell, a canine NK-cell or a human NK-cell.

In certain embodiments, methods of producing HLA-DR CAR expressing cells are disclosed comprising, or alternatively consisting essentially of: (i) transducing a population of isolated cells with a nucleic acid sequence encoding a HLA-DR CAR and (ii) selecting a subpopulation of cells that have been successfully transduced with said nucleic acid sequence of step (i). In some embodiments, the isolated cells are T-cells, an animal T-cell, a mammalian T-cell, a feline T-cell, a canine T-cell or a human T-cell, thereby producing HLA-DR CAR T-cells. In certain embodiments, the isolated cell is an NK-cell, e.g., an animal NK-cell, a mammalian NK-cell, a feline NK-cell, a canine NK-cell or a human NK-cell, thereby producing HLA-DR CAR NK-cells.

Sources of Isolated Cells.

Prior to expansion and genetic modification of the cells disclosed herein, cells may be obtained from a subject—for instance, in embodiments involving autologous therapy—or a commercially available culture.

Cells can be obtained from a number of sources in a subject, including peripheral blood mononuclear cells, bone marrow, lymph node tissue, cord blood, thymus tissue, tissue from a site of infection, ascites, pleural effusion, spleen tissue, and tumors.

Methods of isolating relevant cells are well known in the art and can be readily adapted to the present application; an exemplary method is described in the examples below. Isolation methods for use in relation to this disclosure include, but are not limited to Life Technologies Dynabeads® system; STEMcell Technologies EasySeP™, RoboSep™, RosetteSeP™, SepMate™; Miltenyi Biotec MACS™ cell separation kits, and other commercially available cell separation and isolation kits. Particular subpopulations of immune cells may be isolated through the use of beads or other binding agents available in such kits specific to unique cell surface markers. For example, MACS™ CD4+ and CD8+ MicroBeads may be used to isolate CD4+ and CD8+ T-cells Alternatively, cells may be obtained through commercially available cell cultures, including but not limited to, for T-cells, lines BCL2 (AAA) Jurkat (ATCC® CRL-2902™) BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™); for NK cells, lines NK-92 (ATCC® CRL-2407™), NK-92MI (ATCC® CRL-2408™).

Vectors.

CARs may be prepared using vectors. Aspects of the present disclosure relate to an isolated nucleic acid sequence encoding a HLA-DR CAR and vectors comprising, or alternatively consisting essentially of, or yet further consisting of, an isolated nucleic acid sequence encoding the CAR and its complement and equivalents of each thereof.

In some embodiments, the isolated nucleic acid sequence encodes for a CAR comprising, or alternatively consisting essentially of, or yet further consisting of an antigen binding domain of an anti-HLA-DR antibody, a CD8 α hinge domain, a CD8 α transmembrane domain, a CD28 costimulatory signaling region and/or a 4-1BB costimulatory signaling region, and a CD3 zeta signaling domain. In specific embodiments, the isolated nucleic acid sequence comprises, or alternatively consisting essentially thereof, or yet further consisting of, sequences encoding (a) an antigen binding domain of an anti-HLA-DR antibody followed by (b) a CD8 α hinge domain, (c) a CD8 α transmembrane domain followed by (d) a CD28 costimulatory signaling region and/or a 4-1BB costimulatory signaling region followed by (e) a CD3 zeta signaling domain.

In some embodiments, the isolated nucleic acid sequence comprises, or alternatively consists essentially thereof, or yet further consists of, a Kozak consensus sequence upstream of the sequence encoding the antigen binding domain of the anti-HLA-DR antibody. In some embodiments, the isolated nucleic acid comprises a polynucleotide conferring antibiotic resistance.

In some embodiments, the isolated nucleic acid sequence is comprised in a vector. In certain embodiments, the vector is a plasmid. In other embodiments, the vector is a viral vector. In specific embodiments, the vector is a lentiviral vector.

The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Methods for producing cells comprising vectors and/or exogenous nucleic acids are well-known in the art. See, for example, Sambrook et al. (2001) *Molecular Cloning: A Laboratory Manual*, Cold Spring Harbor Laboratory, New York).

In one aspect, the term "vector" intends a recombinant vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type lentivirus. Examples of such, include without limitation, human immunodeficiency virus (HIV), equine infectious anemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the disclosure need not be confined to the components of a particular virus. The viral vector may comprise components derived from two or more different viruses, and may also comprise synthetic components. Vector components can be manipulated to obtain desired characteristics, such as target cell specificity.

The recombinant vectors of this disclosure are derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,07,993; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5' end of the RNA. The sizes of the three elements can vary considerably among different retroviruses. For the viral genome. and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

Retroviral vectors for use in this disclosure include, but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charité Medical School, Institute of Virology (CBF), Berlin, Germany.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Activation and Expansion of Cells. Whether prior to or after genetic modification of the cells to express a desirable CAR, the cells can be activated and expanded using generally known methods such as those described in U.S. Pat. Nos. 6,352,694; 6,534,055; 6,905,680; 6,692,964; 5,858, 358; 6,887,466; 6,905,681; 7,144,575; 7,067,318; 7,172, 869; 7,232,566; 7,175,843; 5,883,223; 6,905,874; 6,797,514 and 6,867,041. Stimulation with the HLA-DR antigen ex vivo can activate and expand the selected CAR expressing cell subpopulation. Alternatively, the cells may be activated in vivo by interaction with HLA-DR antigen.

Methods of activating relevant cells are well known in the art and can be readily adapted to the present application; an exemplary method is described in the examples below. Isolation methods for use in relation to this disclosure include, but are not limited to Life Technologies Dynabeads® system activation and expansion kits; BD Biosciences Phosflow™ activation kits, Miltenyi Biotec MACS™ activation/expansion kits, and other commercially available cell kits specific to activation moieties of the relevant cell. Particular subpopulations of immune cells may be activated or expanded through the use of beads or other agents available in such kits. For example, α-CD3/α-CD28 Dynabeads® may be used to activate and expand a population of isolated T-cells III. Methods of Use Therapeutic Application.

Method aspects of the present disclosure relate to methods for inhibiting the growth of a tumor in a subject in need thereof and/or for treating a cancer patient in need thereof. In some embodiments, the tumors/cancer is B-cell lymphoma or leukemia tumors/cancer. In some embodiments, the tumor is a solid tumor, e.g. a carcinoma. In some embodiments, the tumor or cancer expresses HLA-DR. In certain embodiments, these methods comprise, or alternatively consist essentially of, or yet further consist of, administering to the subject or patient an effective amount of an isolated cell. In further embodiments, this isolated cell comprises a HLA-DR CAR. In still further embodiments, the isolated cell is a T cell or an NK cell. In some embodiments, the isolated cell is autologous to the subject or patient being treated. In a further aspect, the tumor expresses HLA-DR antigen and the subject has been selected for the therapy by a diagnostic, such as the one described herein. The therapy can be a first line therapy, a second line therapy, a third line therapy, or a fourth line therapy or any additional therapy as determined by the treating physician. They can be combined with other therapies and administered sequentially or concurrently.

The CAR cells as disclosed herein may be administered either alone or in combination with diluents, other anticancer therapeutics other than the CAR cell, and/or with other components such as cytokines or other cell populations that are immunostimulatory.

Pharmaceutical compositions disclosed herein may be administered in a manner appropriate to the disease to be treated or prevented. The quantity and frequency of administration will be determined by such factors as the condition of the patient, and the type and severity of the patient's disease, although appropriate dosages may be determined by clinical trials.

IV. Carriers

Additional aspects of the disclosure relate to compositions comprising a carrier and one or more of the products—e.g., an isolated cell comprising a HLA-DR CAR, an isolated nucleic acid, a vector, an isolated cell of any anti-HLA-DR antibody or CAR cell, an anti-HLA-DR—described in the embodiments disclosed herein.

Briefly, pharmaceutical compositions disclosed herein including but not limited to any one of the claimed compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

EXAMPLES

The following examples are illustrative of procedures which can be used in various instances in carrying the disclosure into effect.

Example 1—Generation of Mouse Anti-Human HLA-DR Monoclonal Antibodies Antigen

Raji African Burkitt's lymphoma cell nuclei were used as the antigen for producing the Lym-1 antibody. CLL biopsy cell nuclei were used as the antigen for producing the Lym-2 antibody.

Immunization Procedures

Four week old female BALB/c mice purchased from Harlan Laboratories were immunized every two weeks ×4 with $10^7$ nuclei emulsified with Complete Freund's Adjuvant (first and second immunization) or incomplete Freund's Adjuvant (third and fourth immunization). Mice were injected intradermally with a total of $10^7$ nuclei/adjuvant divided into three separate spots on the back of the mice per immunization. Ten days after the last immunization, blood samples were obtained and tittered by ELISA procedures on antigen coated plates. Mice showing the highest titers then received a fifth immunization boost intravenously without adjuvant in which $10^6$ nuclei were injected via the lateral tail vein in a 100 µl solution of sterile Phosphate Buffered Saline.

Generation of Hybridomas

Four days later, these mice were sacrificed and the spleens removed for the hybridoma procedure. After dispersing the splenocytes in a solution of RPMI-1640 medium containing Pen/Strep antibiotics, the splenocytes were fused with murine NSO cells using PEG (Hybri MAX, mol wt 1450, Cat. No: p 7181, Sigma). HAT selection was then used to enable only fused cells to grow. Supernatant from wells with growing hybridoma cells were then screened initially by ELISA against antigen coated plates and secondarily by flow cytometry on HLA-DR positive (Raji) and negative human tumor cell lines (CEM T-cell leukemia). Hybridomas showing a positive and high mean fluorescent index (MFI) were selected for subcloning by limiting dilution methods. Subclones were then retested by flow cytometry, frozen in liquid nitrogen, and expanded in 2 L vessels to before antibody was purified by tandon Protein A or G and ion exchange chromatography methods. Purified antibodies were then vialed and stored at −20° C. until used.

Flow Cytometry Procedures and Data

Screening methods using flow cytometry were performed on HLA-DR positive (Raji) and negative (CEM) cell lines using supernatant from hybridomas found positive by ELISA to antigen coated plates. Those hybridomas producing high mean fluorescent indexes (MFI) were then subcloned and rescreened for selective positivity to HLA-DR. As shown below in FIGS. 1A-1F, Lym-1 and Lym-2 produced high MFI to the HLA-DR expressing Raji cell line with a different profile than B1 antibody. From these data, Lym-1 and Lym-2 were selected to generate CAR-T cells as described below.

Immunohistochemistry with Selected Antibodies

Figures 2A, 2B:
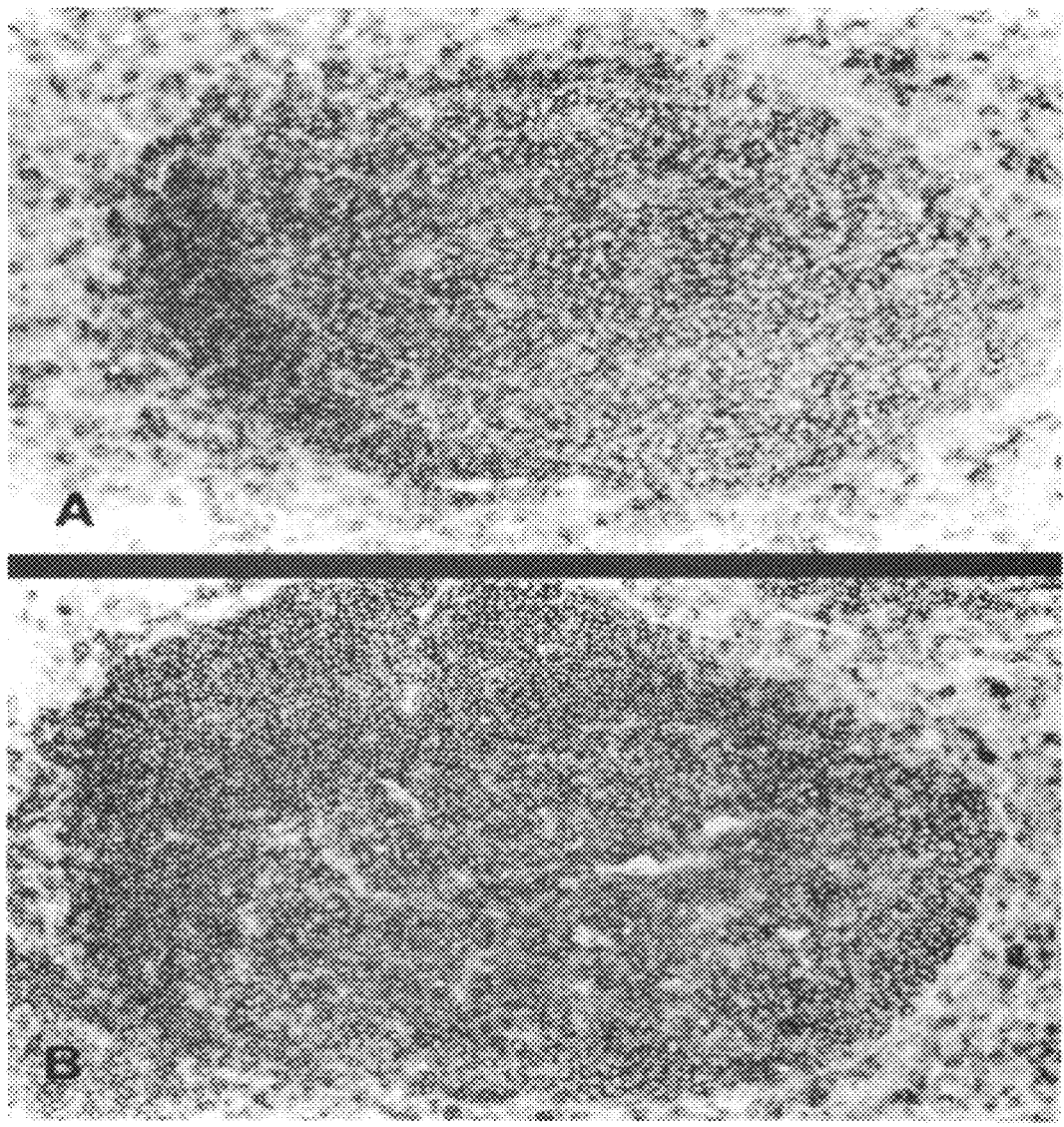
FIGS. 2A-2B show Lym-1 and Lym-2 staining of normal human tonsil demonstrating membrane positivity in B-cell germinal centers. Differences in staining patterns are evident between Lym-1 (FIG. 2A) and Lym-2 (FIG. 2B). Only scattered interfollicular dendritic cells are positive for both antibodies in the T-cell zones (IHC, frozen scions, ×325).

Antibodies Lym-1 and Lym-2 were found to stain HLA-DR positive cells in the germinal centers of human tonsil tissue using standard immunohistochemical procedures and antigen retrieval methods as shown in FIGS. 2A-2B. Staining in thymus, spleen and bone marrow was restricted to B-cell or dendritic cells expressing the HLA-DR antigen (Table 3).

TABLE 3

Reactivity of Lym-1 and Lym-2 with human normal lymphoid and hematopoietic tissues in frozen sections or cytospins

| Organ | Lym-1 | Lym-2 |
| --- | --- | --- |
| Lymph node | | |
| Germinal center | +++[a] | ++ |
| Mantle zone | + | +++ |
| T-cell zones | − | − |
| Interdigitating histiocytes | ++ | ++ |
| Sinus histiocytes | − | − |
| Endothelium | − | − |
| Thymus | | |
| Cortex | − | − |
| Medulla | ++ Dendritic cells | − |
| Spleen | | |
| White pulp | ++ B-cell zones | ++ B-cell zones |
| Red pulp | − | − |

TABLE 3-continued

Reactivity of Lym-1 and Lym-2 with human normal lymphoid and hematopoietic tissues in frozen sections or cytospins

| Organ | Lym-1 | Lym-2 |
|---|---|---|
| Bone marrow | | |
| Myeloid | − | − |
| Erythroid | − | − |
| Megakaryocytes | − | − |

[a]Intensity of immunoperoxidase staining from − to +++.

Figures 3A, 3B:
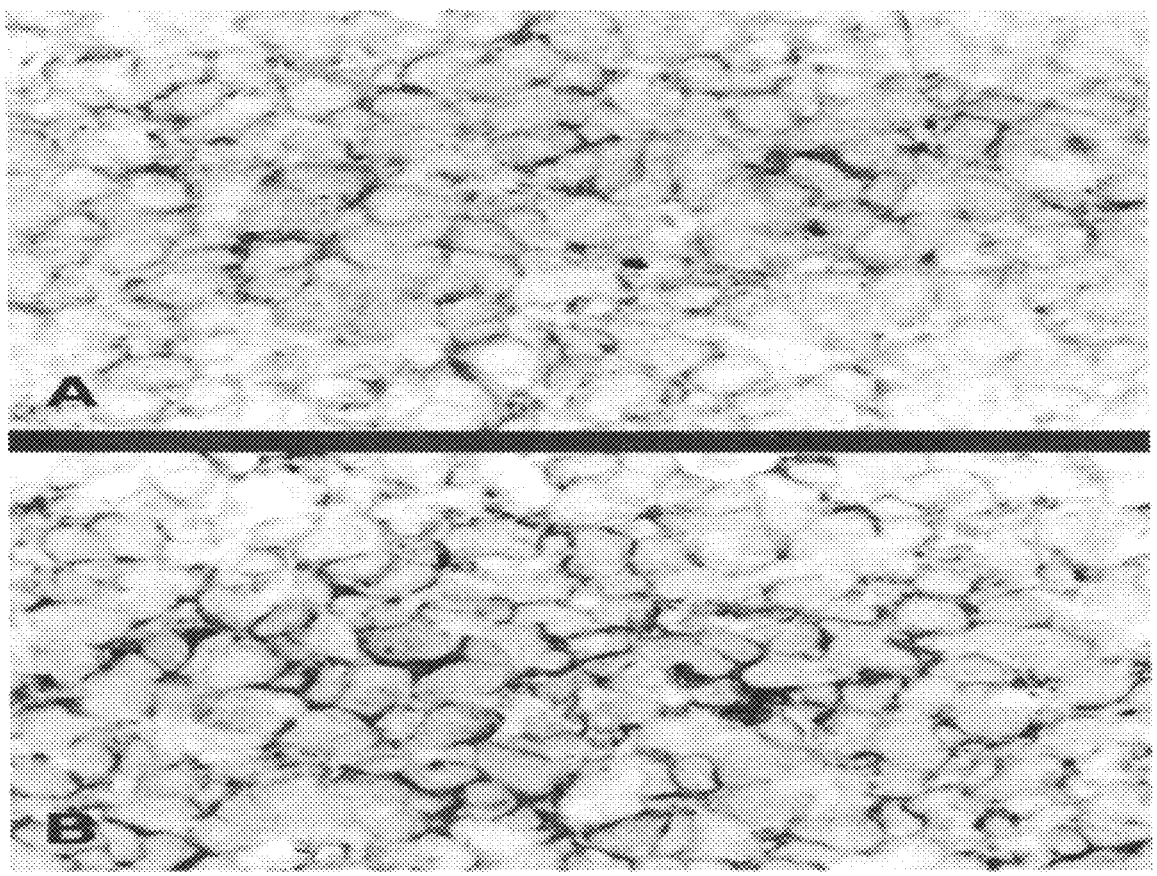
FIGS. 3A and 3B show immunoperoxidase staining of Lym-1 and Lym-2 monoclonal antibodies with an intermediate grade malignant B-cell lymphoma. Immunoperoxidase staining of Lym-1 (FIG. 3A) and Lym-2 (FIG. 3B) monoclonal antibodies with an intermediate grade malignant B-cell lymphoma (frozen sections, ×720). Note prominent membrane staining pattern of majority of cells in the section.

As shown in FIGS. 3A-3B, HLA-DR positivity was seen on the cell membrane of antigen positive tumors such as intermediate grade B-cell lymphomas. Finally, tissue sections from normal tissues and organs showed restricted reactivity to lymphoid B-cells and macrophages of the skin (Table 4). The availability of a companion diagnostic antibody for HLA-DR using immunohistochemistry enables the identification of patients likely to benefit from HLA-DR CAR T-cell therapy in upcoming clinical trials.

TABLE 4

Reactivity of Lym-1 and Lym-2 with normal non-lymphoid tissues in frozen sections

| Tissue | Reactivity | |
|---|---|---|
| | Lym-1 | Lym-2 |
| Adrenal | −[a] | − |
| Brain | − | − |
| Breast | − | − |
| Cervix | − | − |
| Colon | + surface epithelium | − |
| Duodenum | − | − |
| Heart | − | − |
| Kidney | − | − |
| Liver | − | − |
| Lung | − | − |
| Ovary | − | − |
| Pancreas | − | − |
| Salivary glands | − | − |
| Skin | + macrophages only | − |
| Skeletal muscle | − | − |
| Smooth muscle | − | − |
| Stomach | − | − |
| Testis | − | − |
| Thyroid | − | − |

[a]Intensity of immunoperoxidase staining from − to +++.

Live Cell Radioimmunoassay

Using Lym-1 or Lym-2, a panel of human lymphoma and solid tumor cell lines were screened for binding using a live cell radioimmunoassay procedure. For this assay, suspension cultures and solid tumor cell lines which were dislodged from their flasks with EDTA-trypsin were washed twice in cold buffer consisting of PBS, bovine serum albumin (1 mg/ml), and 0.02% sodium azide. Cells ($5 \times 10^5$) resuspended in 100 μl of wash buffer were pipetted into microwells pretreated overnight with BSA (10 mg/ml) in PBS to prevent antibody binding to the wells. Lym-1 or Lym-2 supernatant were then added (100 μl/well) for a 30 minute incubation period with continuous shaking using a microshaker apparatus for 96 well plates at room temperature. After 4 washes, 100,000 cpm of I-125 goat anti-mouse IgG was then added in 100 μl and incubated with the cells for an additional 30 minute incubation with continuous shaking. After 4 final washes, the wells were counted in a gamma counter to determine antibody binding to each cell preparation. The results of these studies showed that for a large panel of human lymphoma and leukemia biopsies, reactivity of Lym-1 and Lym-2 was restricted to tumors of B-cell but not T-cell origin (Table 5).

TABLE 5

Reactivity of Lym-1 and Lym-2 with human malignant lymphoma and leukemia biopsy specimens

| Diagnosis | Lym-1[a] | Lym-2[a] |
|---|---|---|
| Lymphomas[b] (frozen sections of lymph node biopsies[c]) | | |
| Well-differentiated lymphocytic | 1/3 | 3/3 |
| Poorly differentiated lymphocytic, nodular | 0/2 | 2/2 |
| Poorly differentiated lymphocytic, diffuse | 1/3 | 3/3 |
| Mixed lymphocytic and histiocytic | 8/9 | 7/9 |
| Histiocytic (B-cell) | 12/17 | 12/17 |
| T-cell | 0/2 | 0/2 |
| Leukemias (cytospins of peripheral blood[d]) Chronic lymphocytic | | |
| B-cell type | 4/10 | 8/10 |
| T-cell type | 0/5 | 0/5 |

[a]Positive/total.
[b]Rappaport classification.
[c]Immunoperoxidase technique.
[d]Indirect immunofluorescence.

Consistent with these results, Lym-1 and Lym-2 was found to bind to a select number of human lymphoma and leukemia cell lines as shown in Table 6.

TABLE 6

Reactivity of Lym-1 and Lym-2 with human malignant lymphoma cell lines by live cell radioimmunoassay

| Cell Line | Lym-1 | Lym-2 |
|---|---|---|
| Burkitt's Lymphoma | | |
| Raji | ++++[a] | ++ |
| EB3 | − | − |
| DG-75 | ++++ | ++++ |
| NK-9 | ++ | ++++ |
| AL-1 | − | + |
| Daudi | + | +++ |
| NU-AmB-1 | + | ++ |
| SU-AmB-1 | − | + |
| SU-AmB-2 | − | − |
| RAMOS | − | − |
| Chevallier | ++++ | − |
| B46M | + | + |
| B35M | ++++ | ++++ |
| DND-39 | + | − |
| U-698-M | + | ++ |
| HRIK | − | + |
| Large Cell Lymphoma | | |
| SU-DHL-1 | − | − |
| SU-DHL-2 | − | − |
| SU-DHL-4 | − | ++++ |
| SU-DHL-5 | + | ++ |
| SU-DHL-6 | +++ | +++ |
| SU-DHL-7 | + | − |
| SU-DHL-8 | + | − |
| SU-DHL-9 | + | + |
| SU-DHL-10 | − | ++++ |
| SU-DHL-16 | − | − |
| NU-DHL-1 | ++++ | − |
| U-937 | − | − |
| Undifferentiated lymphoma | | |
| NU-DUL-1 | − | + |

[a]−, <2,000 cpm; +, 2,000-6,000 cpm; ++, 6,000-10,000 cpm; +++, 10,000-15,000 cpm; ++++, >15,000 cpm.

By contrast, Lym-1 and Lym-2 was not found to bind to 35 human solid tumor cell lines using live cell radioimmunoassay procedures described above (Table 7).

TABLE 7

Reactivity of Lym-1 and Lym-2 with 35 human solid tumor cell lines by live cell radioimmunoassay

| Cell line | Derivation | Lym-1 | Lym-2 |
|---|---|---|---|
| 734B | Breast carcinoma | −[a] | − |
| 578T | Breast carcinoma | − | − |
| C-399 | Colon carcinoma | − | − |
| Hutu-80 | Colon carcinoma | − | − |
| HT-29 | Colon carcinoma | − | − |
| HeLa | Cervical carcinoma | − | − |
| SW 733 | Papillary carcinoma of bladder | − | − |
| SW 780 | Transitional cell carcinoma of bladder | − | − |
| SW 451 | Squamous cell carcinoma of esophagus | − | − |
| SW 579 | Squamous cell carcinoma of thyroid | − | − |
| SW 156 | Hypernephroma | − | − |
| 60 | Small cell carcinoma of lung | − | − |
| 464 | Small cell carcinoma of lung | − | − |
| NCI-H69 | Small cell carcinoma of lung | − | − |
| 125 | Adenocarcinoma of lung | − | − |
| A427 | Adenocarcinoma of lung | − | − |
| A549 | Adenocarcinoma of lung | − | − |
| SW 1503 | Mesothelioma | − | − |
| BM 166 | Neuroblastoma | − | − |
| IMR-5 | Neuroblastoma | − | − |
| Y79 | Retinoblastoma | − | − |
| A172 | Astrocytoma | − | − |
| SW 608 | Astrocytoma | − | − |
| U118 MG | Glioblastoma | − | − |
| NU-04 | Glioblastoma | − | − |
| CaCl 74-36 | Melanoma | − | − |
| Colo 38 | Melanoma | − | − |
| SW 872 | Liposarcoma | − | − |
| HS 919 | Liposarcoma | − | − |
| SW 1045 | Synovial sarcoma | − | − |
| SW 80 | Rhabdomyosarcoma | − | − |
| SW 1353 | Chondrosarcoma | − | − |
| 4-998 | Osteogenic sarcoma | − | − |
| 4-906 | Osteogenic sarcoma | − | − |
| SU-CCS-1 | Clear cell sarcoma | − | − |

[a]−, <2,000 cpm; +, 2,000-6,000 cpm; ++, 6,000-10,000 cpm; +++, 10,000-15,000 cpm; ++++, >15,000 cpm.

Figure 4A:
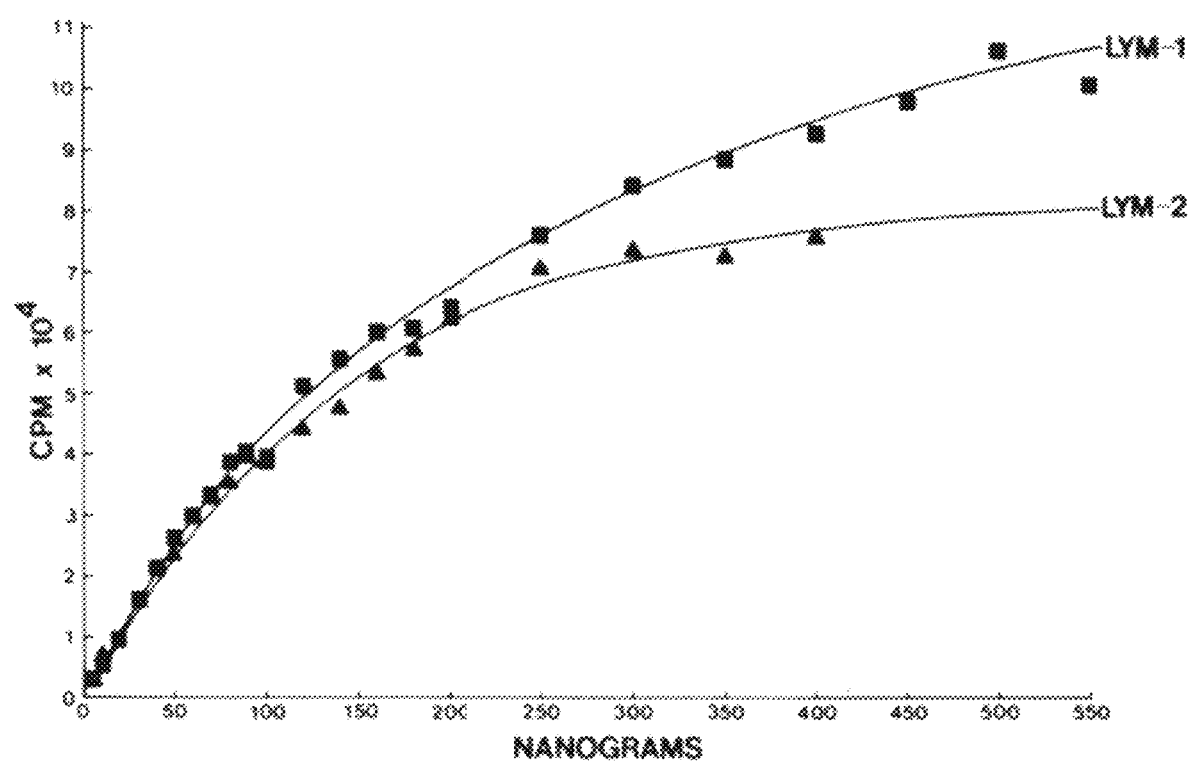
FIGS. 4A-4C show binding profiles and Scatchard Plots of (FIG. 4A) Binding profiles of Lym-1 monoclonal antibodies to Raji cells and Lym-2 monoclonal antibodies to ARH-77 cells.
Figure 4B:
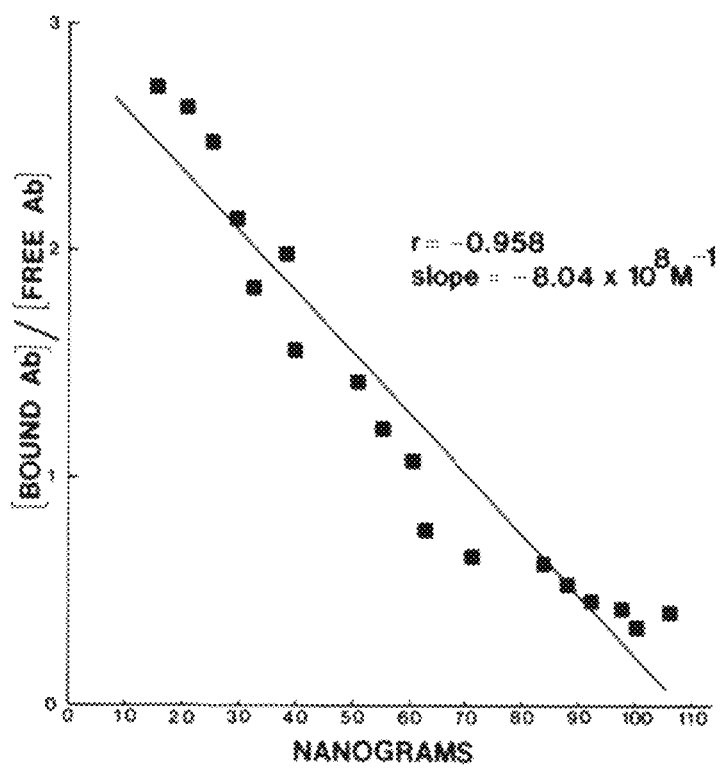
Figure 4C:
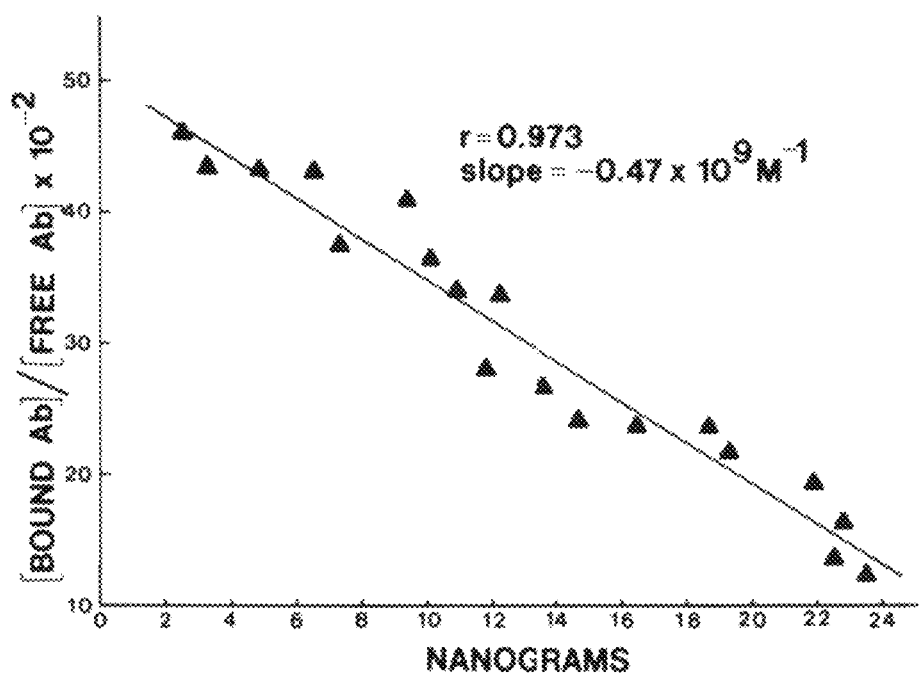
Figures 5A, 5B:
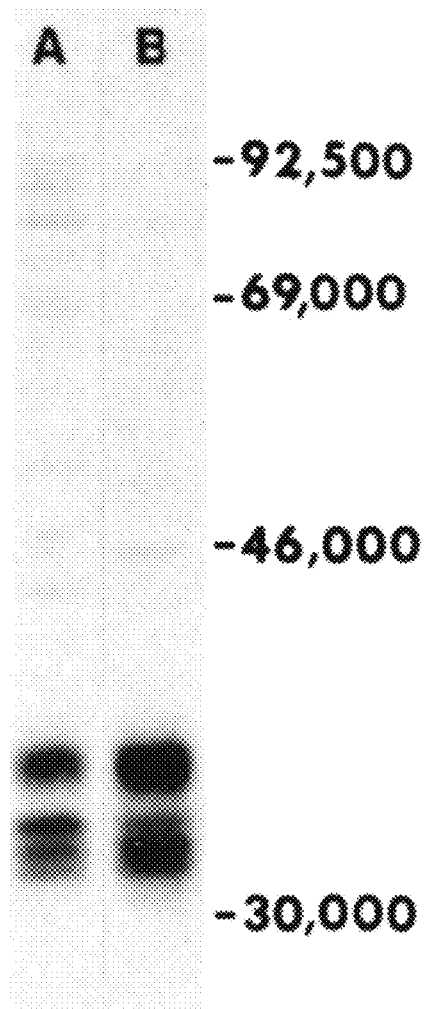
FIGS. 5A and 5B show immunoprecipitation of $^{35}$S-methionine and $^{14}$C-leucine-labeled Raji proteins by Lym-1 (FIG. 5A) and SC-2 anti-HLA-DR antibody (FIG. 5B).

Binding Profiles of Lym-1 and Lym-2 Antibodies and Identification of Lym-1 Antigen Binding profiles and Scatchard plot analyses of Lym-1 binding with Raji cells is shown in FIG. 4A. Likewise, Scatchard plot analyses of Lym-2 binding with the ARH-77 myeloma cell line are shown in FIG. 4B. These data demonstrated that both antibodies have $10^8$ $M^{-1}$ binding affinities to antigen positive tumor cell lines. As shown in Table 8, when compared to normal peripheral blood B cells, there was a two to four-fold decrease in binding affinities compared to that seen with tumor cells. In addition, metabolic labeling of Raji cells with $^{35}$S-methionine and $^{14}$C-leucine showed the characteristic banding pattern seen for HLA-DR (FIGS. 5A-5B). As a control, the SC-1 anti-HLA-DR antibody was used in parallel and gave the same banding pattern with identical protein molecular weights by SDS-gel electrophoresis.

TABLE 6

Avidity constants of Lym-1 and Lym-2 using target tumor cell lines (Raji, ARH-77) and tonsil lymphocytes

| Monoclonal antibody | Tumor cell line | Tonsil |
|---|---|---|
| Lym-1 | $4.02 \times 10^8$ $M^{-1}$ | $0.88 \times 10^8$ $M^{-1}$ |
| Lym-2 | $2.33 \times 10^8$ $M^{-1}$ | $1.23 \times 10^8$ $M^{-1}$ |

Example 2—Generation of HLA-DR CAR T-Cells

Construction and Synthesis Single Chain HLA-DR Antibody Genes

Figure 6A:
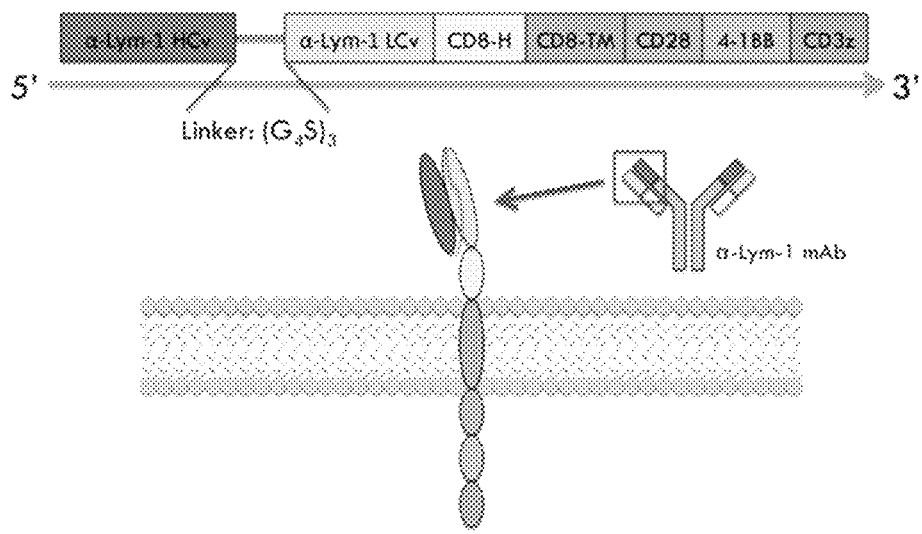
FIGS. 6A and 6B show a construction schematic of (FIG. 6A) Lym-1 and (FIG. 6B) Lym-2 CAR T-cells for immunotherapy.
Figure 6B:
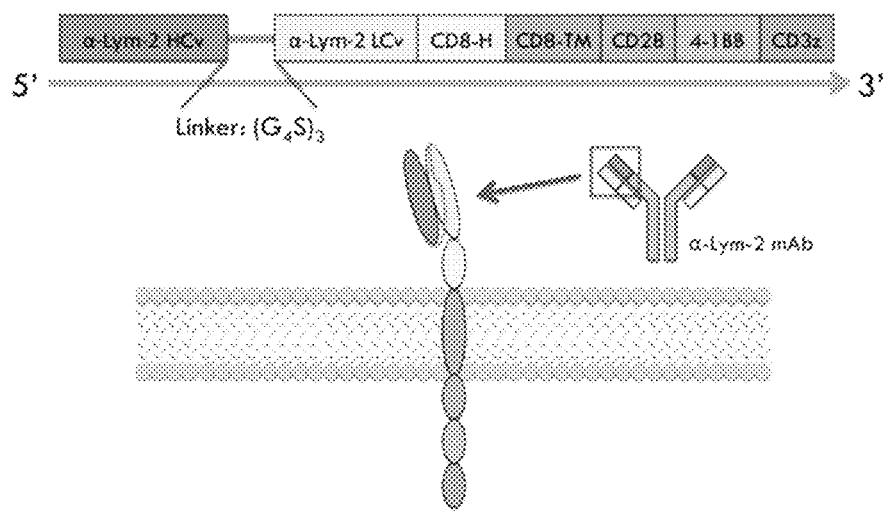

The DNA sequences for 2 high binding anti-HLA-DR antibodies generated in the laboratory (Lym-1 and Lym-2) are obtained from MCLAB (South San Francisco, Calif.). Both antibodies are tested to determine which one produces the most effective CAR in assays described below. As shown below, second or third (FIG. 6) generation CAR vectors are constructed consisting of the following tandem genes: a kozak consensus sequence; the CD8 signal peptide; the anti-HLA-DR heavy chain variable region; a (Glycine4Serine)3 flexible polypeptide linker (SEQ ID NO: 51); the respective anti-HLA-DR light chain variable region; CD8 hinge and transmembrane domains; and the CD28, 4-1BB, and CD3ζ intracellular co-stimulatory signaling domains. Hinge, transmembrane, and signaling domain DNA sequences are ascertained from a patent by Carl June (see U.S. Patent Application Publication No. 2013/0287748 A1). Anti-HLA-DR CAR genes are synthesized by Genewiz, Inc. (South Plainfield, N.J.) within a pUC57 vector backbone containing the bla gene, which confers ampicillin resistance to the vector host.

Subcloning of CAR Genes into Lentiviral Plasmids

NovaBlue Singles™ chemically-competent E. coli cells are transformed with anti-HLA-DR plasmid cDNA. Following growth of the transformed E. coli cells, the CAR plasmids are purified and digested with the appropriate restriction enzymes to be inserted into an HIV-1-based lentiviral vector containing HIV-1 long terminal repeats (LTRs), packaging signal (Ψ), EF1α promoter, internal ribosome entry site (IRES), and woodchuck hepatitis virus post-transcriptional regulatory element (WPRE) via overnight $T_4$ DNA ligase reaction (New England Biosciences; Ipswich, Mass.). NovaBlue Singles™ chemically-competent E. coli cells are then transformed with the resulting anti-HLA-DR containing lentiviral plasmid.

Production of Lentiviral Particles

Prior to transfection, HEK293T cells are seeded at $4.0 \times 10^6$ cells/100 mm tissue-culture-treated plate in 10 mL complete-Tet-DMEM and incubated overnight at 37° C. in a humidified 5% $CO_2$ incubator. Once 80-90% confluent, HEK293T cells are co-transfected with CAR-gene lentiviral plasmids and lentiviral packaging plasmids containing genes necessary to form lentiviral envelope & capsid components, in addition to a proprietary reaction buffer and polymer to facilitate the formation of plasmid-containing nanoparticles that bind HEK293T cells. After incubating transfected-HEK293T cell cultures for 4 hours at 37° C., the transfection medium is replaced with 10 mL fresh complete Tet DMEM. HEK293T cells are then incubated for an additional 48 hours, after which cell supernatants are harvested and tested for lentiviral particles via sandwich ELISA against p24, the main lentiviral capsid protein. Lentivirus-containing supernatants are aliquoted and stored at −80° C. until use for transduction of target CD4$^+$ and CD8$^+$ T cells.

Purification, Activation, and Enrichment of Human CD4$^+$ and CD8$^+$ Peripheral Blood T-Cells Peripheral blood mononuclear cells (PBMCs) are enriched by density gradient centrifugation with Ficoll-Paque Plus (GE Healthcare; Little Chalfont, Buckinghamshire, UK) are recovered and washed by centrifugation with PBS containing 0.5% bovine serum albumin (BSA) and 2 mM EDTA. MACS CD4$^+$ and CD8$^+$ MicroBeads (Miltenyi Biotec; San Diego, Calif.) kits are used to isolate these human T-cell subsets using magnetically activated LS columns to positive select for CD4+ and CD8+ T-cells. Magnetically-bound T-cells are then removed from the magnetic MACS separator, flushed from the LS column, and washed in fresh complete medium. The purity of CD4+ and CD8+ T-cell populations are assessed by flow cytometry using Life Technologies Acoustic Attune® Cytometer, and are enriched by Fluorescence-Activated Cell Sorting performed at USC's flow cytometry core facilities if needed. CD4+ and CD8+ T-cells are maintained at a density of $1.0\times10^6$ cells/mL in complete medium supplemented with 100 IU/mL IL-2 in a suitable cell culture vessel, to which α-CD3/α-CD28 Human T-cell Dynabeads (Life Technologies; Carslbad, Calif.) are added to activate cultured T cells. T-cells are incubated at 37° C. in a 5% $CO_2$ incubator for 2 days prior to transduction with CAR-lentiviral particles.

Lentiviral Transduction of CD4+ CD8+ T-Cells

Activated T-cells are collected and dead cells are removed by Ficoll-Hypaque density gradient centrifugation or the use of MACS Dead Cell Removal Kit (Miltenyi Biotec; San Diego, Calif.). In a 6-well plate, activated T-cells are plated at a concentration of $1.0\times10^6$ cells/mL complete medium. To various wells, HLA-DR CAR-containing lentiviral particles are added to cell suspensions at varying multiplicity of infections (MOIs), such as 1, 5, 10, and 50. Polybrene, a cationic polymer that aids transduction by facilitating interaction between lentiviral particles and the target cell surface, are added at a final concentration of 4 μg/mL. Plates are centrifuged at 800×g for 1 hr at 32° C. Following centrifugation, lentivirus-containing medium are aspirated and cell pellets are resuspended in fresh complete medium with 100 IU/mL IL-2. Cells are placed in a 5% $CO_2$ humidified incubator at 37° C. overnight. Three days post-transduction, cells are pelleted and resuspended in fresh complete medium with IL-2 and 400 μg/mL Geneticin (G418 sulfate) (Life Technologies; Carlsbad, Calif.). HLA-DR CAR modified T-cells are assessed by flow cytometry and southern blot analysis to demonstrate successful transduction procedures. Prior to in vitro and in vivo assays, HLA-DR CAR T-cells are enriched by FACS and mixed 1:1 for the in vivo studies.

In Vitro Assessment of CAR Efficacy by Calcein-Release Cytotoxicity Assays

HLA-DR antigen positive and negative human cell lines are collected, washed, and resuspended in complete medium at a concentration of $1.0\times10^6$ cells/mL. Calcein-acetoxymethyl (AM) are added to target cell samples at 15 which are then incubated at 37° C. in a 5% $CO_2$ humidified incubator for 30 minutes. Dyed positive and negative target cells are washed twice and resuspended in complete medium by centrifugation and added to a 96-well plate at $1.0\times10^4$ cells/well. HLA-DR CAR T-cells are added to the plate in complete medium at effector-to-target cell ratios of 50:1, 5:1, and 1:1. Dyed-target cells suspended in complete medium and complete medium with 2% triton X-100 serve as spontaneous and maximal release controls, respectively. The plates are centrifuged at 365×g and 20° C. for 2 minutes before being placed back in the incubator 3 hours. The plates are then centrifuged 10 minutes and cell supernatants are aliquoted to respective wells on a black polystyrene 96-well plate and assessed for fluorescence on a Bio-Tek® Synergy™ HT microplate reader at excitation and emissions of 485/20 nm and 528/20 nm, respectively.

Quantification of Human Cytokines by Luminex Bioassay

Supernatants of HLA-DR CAR modified T-cells and HLA-DR positive and negative tumor cell lines are measured for cytokine secretion as a measure of CAR T-cell activation using standard procedures performed routinely in the laboratory. Data are compared to medium alone and to cultures using non-activated human T-cells to identify background activity. The concentration of IL-2, IFN-g, IL-12, and other pertinent cytokines are measured over time during the incubation process.

In Vivo Assessment of CAR T-Cell Efficacy in Two Xenograft HLA-DR Positive Cancer Models HLA-DR CAR T-cells are further evaluated in vivo using two different human tumor cell line xenograft tumor models. For both, solid tumors are established subcutaneously in 6-8 week old female nude mice by injection of $5\times10^6$ HLA-DR positive or HLA-DR negative solid tumor cell lines. When the tumors reach 0.5 cm in diameter, groups of mice (n=5) are treated intravenously with 1 or $3\times10^7$ human T-cells as negative controls or HLA-DR CAR T-cells constructed from the most active HLA-DR antibodies based upon the in vitro study results. Tumor volumes are then measured by caliper 3×/week and volume growth curves are generated to demonstrate the effectiveness of experimental treatments over controls.

HLA-DR is found to be an outstanding target for CAR T-cell development.

Example 3—Lym-1 CAR Cells

Construction of the CAR Lentiviral Constructs

Figure 7:
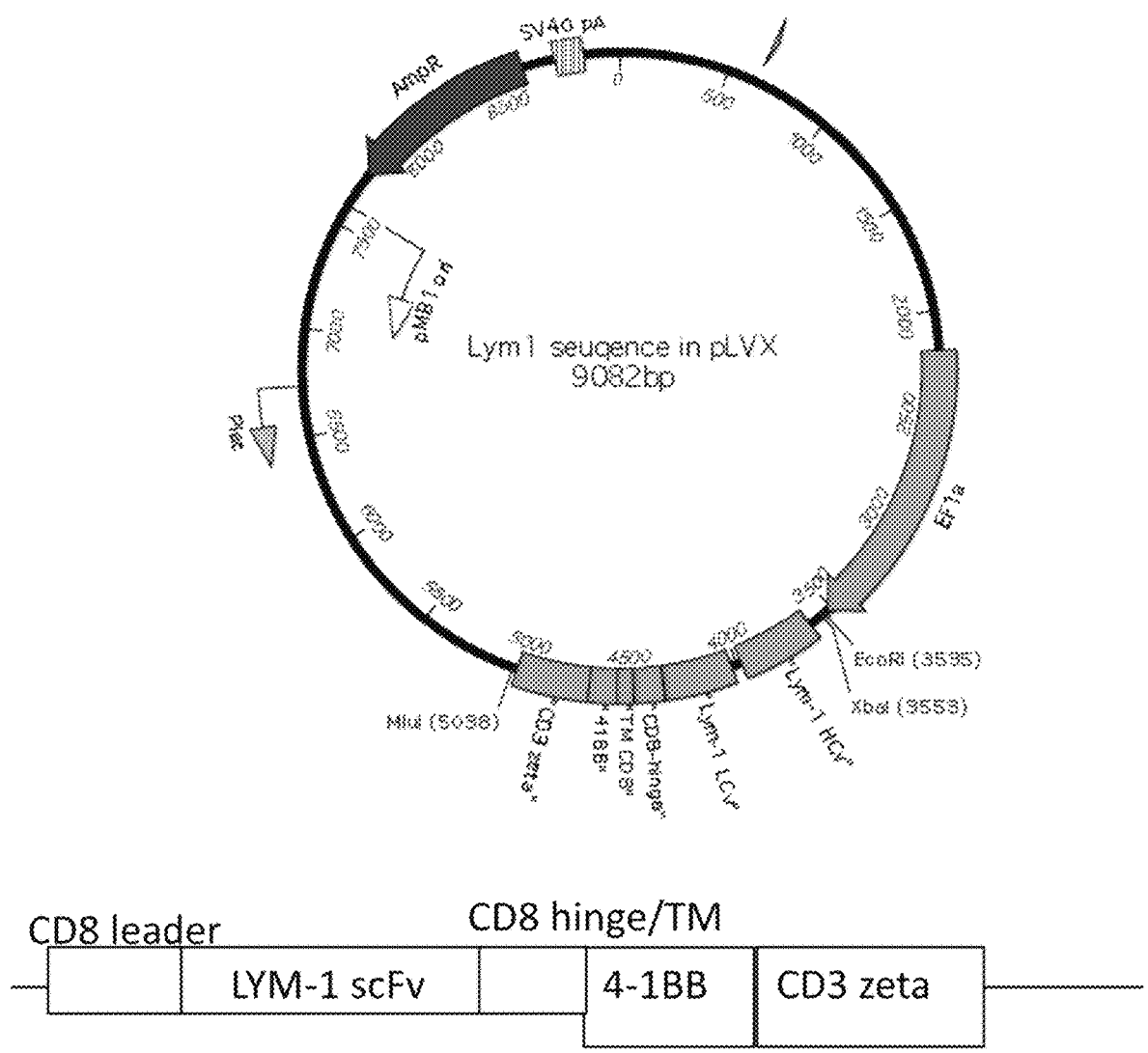
FIG. 7 depicts a schematic a non-limiting exemplary Lym-1 gene-transfer vector and transgene. The backbone of the gene transfer vector is an HIV-based, bicistronic lentiviral vector, pLVX-IRES-ZsGreen containing HIV-1 5' and 3' long terminal repeats (LTRs), packaging signal (Ψ), EF1α promoter, internal ribosome entry site (IRES), ZsGreen, a green fluorescent protein, woodchuck hepatitis virus post-transcriptional regulatory element (WPRE), and simian virus 40 origin (SV40). Constitutive expression of the transgene comprising of aCD8 leader sequence, a scFV specific to Lym-1, a CD8 hinge and transmembrane region and 4-1BB and CD3ζ signaling domain, is insured by the presence of the EF-1α promoter. Expression of the detection protein, ZsGreen is carried out by the IRES region. Integration of the vector can be assayed by the presence of ZsGreen in the cells, via fluorescent microscopy.

The Lym-1 CAR vector contains a CD8 leader sequence followed by the extracellular antigen binding moiety or scFV, which binds specifically to Lym-1 antigen. The scFV is connected via a CD8 hinge region to the cytoplasmic signaling domain, comprised of the CD8 transmembrane region, and the signaling domains from 4-1BB and CD3ζ (FIG. 7). The CAR sequence including the signaling domains, were synthetically synthesized by Genewiz Gene Synthesis services (Piscataway, N.J.). The plasmids are purified and digested with the appropriate restriction enzymes to be inserted into an HIV-1-based lentiviral vector (pLVX-IRES-ZsGreen, Clontech, Signal Hill, Calif.) containing HIV-1 5' and 3' long terminal repeats (LTRs), packaging signal (Ψ), EF1α promoter, internal ribosome entry site (IRES), woodchuck hepatitis virus post-transcriptional regulatory element (WPRE) and simian virus 40 origin (SV40) via overnight T4 DNA ligase reaction (New England Biosciences; Ipswich, Mass.), followed by deletion of the IRES-ZsGreen using restriction enzyme digestion and ligation with T4 DNA ligase. NovaBlue Singles™ chemically-competent E. coli cells are then transformed with the resulting CAR-containing lentiviral plasmid.

Production of Lentiviral Particles

Prior to transfection, HEK 293T cells are seeded at 4.0×106 cells in a 150 cm2 tissue-culture-treated flask in 20 mL DMEM supplemented with 10% dialyzed FCS and incubated overnight at 37° C. in a humidified 5% CO2 incubator. Once 80-90% confluent, HEK 293T cells are incubated in 20 ml DMEM supplemented with 1-% dialyzed FCS without penicillin/streptamycin for two hours in at 37° C. in a humidified 5% CO2 incubator. HEK293T cells are co-transfected with the CAR plasmid and lentiviral packaging plasmids containing genes necessary to form the lentiviral envelope & capsid components. A proprietary reaction buffer and polymer to facilitate the formation of plasmid-containing nanoparticles that bind HEK 293T cells are also added. After incubating the transfected-HEK 293T cell cultures for 24 hours at 37° C., the transfection medium is replaced with 20 mL fresh complete DMEM. Lentivirus supernatants are collected every 24 hours for three days and the supernatants are centrifuged at 1,250 rpm for 5 mins at 4° C., followed by filter sterilization and centrifugation in an ultracentrifuge at 20,000 g for 2 hrs at 4° C. The concentrated lentivirus is re-suspended in PBA containing 7% trehalose and 1% BSA. The lentivirus is then aliquoted and stored at −80° C. until use for transduction of target CD4+ and CD8+ T cells. The cell supernatants harvested after 24 hours are tested for lentiviral particles via sandwich ELISA against p24, the main lentiviral capsid protein. Transfection efficiency was estimated between 20%-50%, by staining with a biotin-labeled Protein L antibody (Genscript, Piscataway, N.J.), followed by incubation with a streptavidin conjugated to PE, and detection by FACS analysis.

Purification, Activation, and Enrichment of Human CD4+ and CD8+ Peripheral Blood T-Cells Peripheral blood mononuclear cells (PBMCs) enriched by density gradient centrifugation with Ficoll-Paque Plus (GE Healthcare; Little Chalfont, Buckinghamshire, UK) are recovered and washed by centrifugation with PBS containing 0.5% bovine serum albumin (BSA) and 2 mM EDTA. T-cell enrichment kits (Stem Cell Technologies) are used to isolate these human T-cell subsets magnetically using negative selection for CD4+ and CD8+ T-cells. The purity of CD4+ and CD8+ T-cell populations is assessed by flow cytometry using Life Technologies Acoustic Attune® Cytometer, and are enriched by Fluorescence-Activated Cell Sorting. CD4+ and CD8+ T-cells mixed 1:1 are maintained at a density of $1.0 \times 10^6$ cells/mL in complete 50% Click's medium/50% RPMI-1640 medium supplemented with 100 IU/mL IL-2 in a suitable cell culture vessel, to which α-CD3/α-CD28 Human T-cell activator beads (Stem Cell Technologies) are added to activate cultured T cells. T-cells are then incubated at 37° C. in a 5% $CO_2$ incubator for 2 days prior to transduction with CAR lentiviral particles.

Lentiviral Transduction of CD4+CD8+ T-Cells

Activated T-cells are collected and dead cells are removed by Ficoll-Hypaque density gradient centrifugation or the use of MACS Dead Cell Removal Kit (Miltenyi Biotec; San Diego, Calif.). In a 6-well plate, activated T-cells will be plated at a concentration of $1.0 \times 10^6$ cells/mL in complete medium. Cells will be transduced with the lentiviral particles supplemented with Lentiblast, a transfection aid (Oz Biosciences, San Diego, Calif.) to the cells. Transduced cells were incubated for 24 hours at 37° C. in a humidified 5% $CO_2$ incubator. The cells are spun down and the media changed, followed by addition of the T-cell activator beads (Stem Cell Technologies, San Diego, Calif.).

Detection of Lym-1 CAR Expression by Flow Cytometry

Seven days after Lentivirus transduction, primary T-cells are washed 3× using wash buffer (4% BSA in PBS). Cells are incubated with Biotein-Protein L (2 ug, Genscript, Piscataway, N.J.) at 4° C. for 45 min. Cells are again washed 3× with wash buffer, followed by incubation with 2 ul of Streptavidin-PE (BD Sciences, La Jolla, Calif.) at 4° C. for 45 min. Cells are washed 3× and analyzed using flow cytometry (Attune Cytometer, Applied Biosciences, Carlsbad, Calif.).

Cell Cytotoxicity Assays

Cytotoxicity of the Lym-1 CAR T-cells are determined using the lactate dehydrogenase (LDH) cytotoxicity kit (Thermo Scientific, Carlsbad, Calif.). Activated T-cells are collected and $1 \times 10^6$ cells are transduced with the Lym-1 CAR lentiviral construct as described above. Cells are activated used the T-cell activator beads (Stem Cell Technologies, San Diego, Calif.) for two days prior to cytotoxicity assays. The optimal number of target cells is determined as per the manufacturer's protocol. For the assays, the appropriate target cells are plated in triplicate in a 96 well plate for 24 hours at 37° C. in a 5% $CO_2$ incubator, followed by addition of activated CAR T-cells in ratios of 20:1, 10:1, 5:1 and 1:1, and incubated for 24 hours at 37° C. in a 5% $CO_2$ incubator. Cells are lysed at 37° C. for 45 mins and spun down at 1,250 rpm for 5 minutes. The supernatants are transferred to a fresh 96 well plate, followed by the addition of the reaction mixture for 30 minutes. The reaction is stopped using the stop solution and the plate read at 450 nm with an absorbance correction at 650 nm.

In Vivo Tumor Regression Assay

Foxn1 null mice are injected with immortalized B lymphoma cell line, Raji, which expresses the Lym-1 antigen. Two×$10^6$ Raji cells with $1 \times 10^6$ human fibroblasts in 200 ul of phosphate buffered saline (PBS) are injected into the left flank of pre-irradiated mice (400 rads) to reduce the number of circulating NK cells enabling the heterotransplants to implant at a high frequency. T-cells are activated for 2 days with the αCD3/CD28 activator complex (Stem Cell Technologies, San Diego, Calif.). The activated T-cells are then transduced with Lym-1 CAR lentiviral particles, followed by activation with the αCD3/CD28 activator complex for an additional 2 days. The activated T-cells expressing the Lym-1 CAR ($2.5 \times 10^6$) are injected intravenously via the lateral tail vein into the mice on day 7 after tumor inoculation. Tumor sizes are assessed 3×/week using Vernier calipers and the tumor volumes calculated.

Detection of Lym-1 CAR Expression

Figure 8:
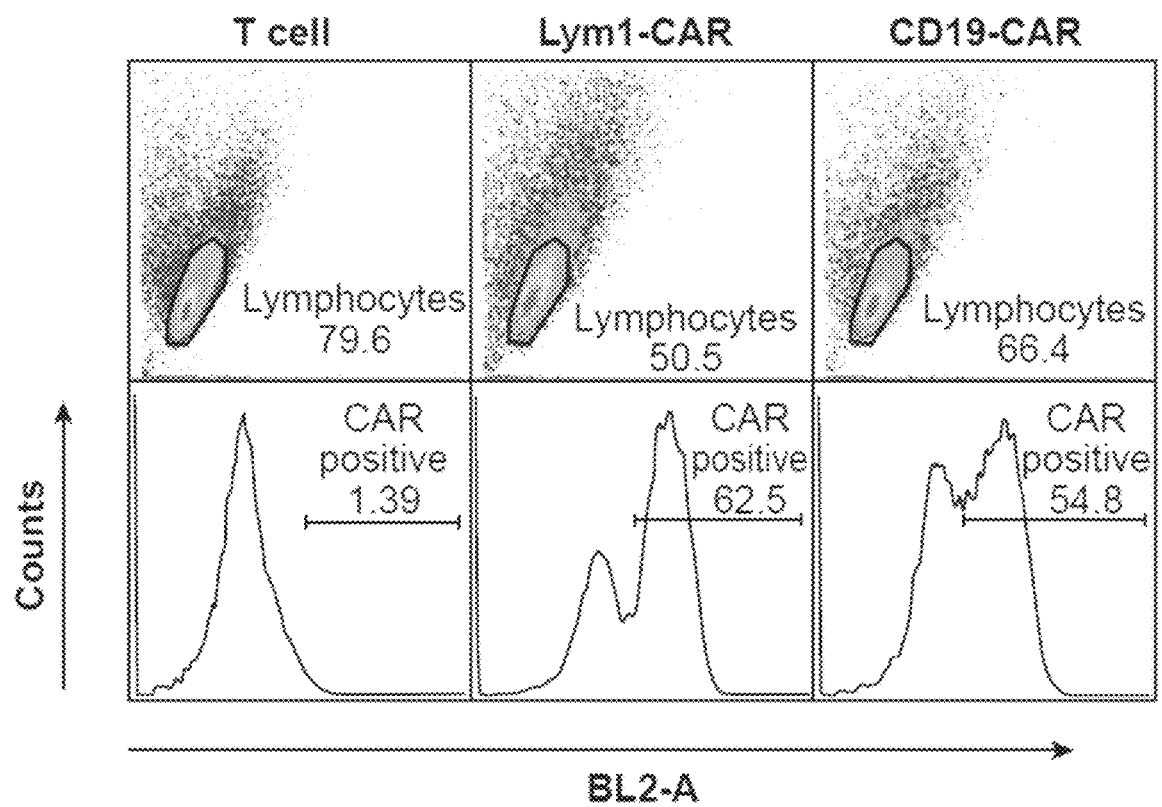
FIG. 8 shows expression of Lym-1 CAR on primary human T-cells. T-cells were transduced with the Lym-1 CAR and stained with Biotein-Protein L, followed by Streptavidin-PE. Cells were analyzed by flow cytometry.
Figure 9:
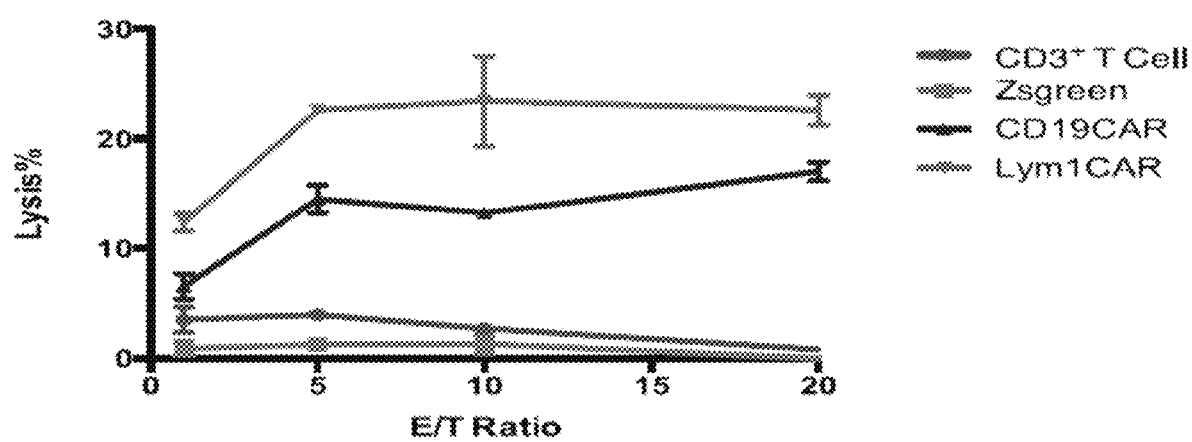
FIG. 9 shows cytotoxicity of the Lym-1-CAR T-cells. Cytotoxicity of the Lym-1 CAR expressing T-cells was determined using an LDH cytotoxicity kit as described in the Methods. Prior to the assay, T-cells were activated using αCD3/CD8 beads (Stem Cell Technologies, 30 ul to 2 ml of media). The activated T-cells were transduced with Lym-1 CAR lentiviral particles, following which the T cells were activated using the αCD3/CD8 beads. Un-transduced, activated T-cells were used as a control. 15,000 Raji cells were plated per well. Lym-1 CAR transduced T cells were added in ratios of 20:1, 10:1, 5:1 and 1:1 to the wells. Each data point represents the average of triplicate measurements.
Figure 10:
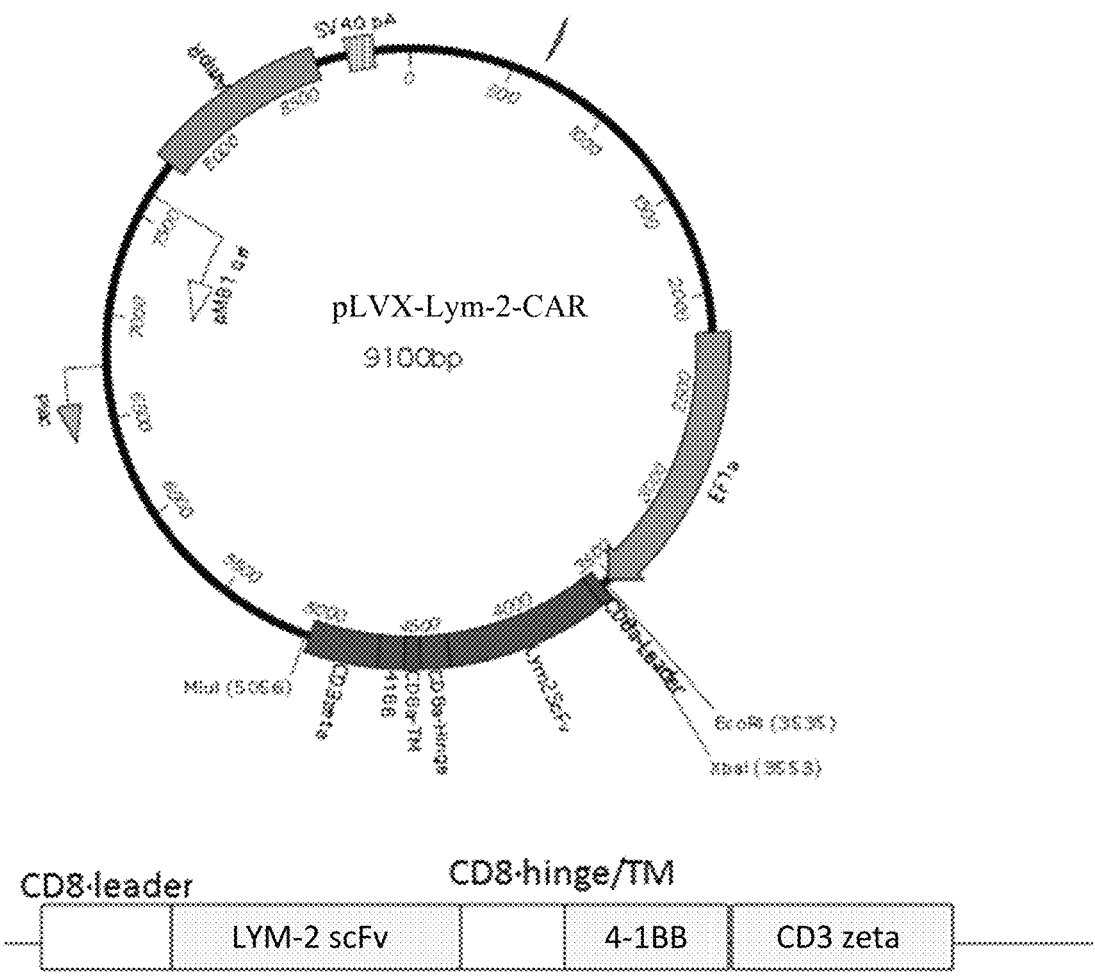
FIG. 10 depicts a schematic a non-limiting exemplary Lym-2 gene-transfer vector and transgene. The backbone of the gene transfer vector is an HIV-based, bicistronic lentiviral vector, pLVX-IRES-ZsGreen containing HIV-1 5' and 3' long terminal repeats (LTRs), packaging signal (Ψ), EF1α promoter, internal ribosome entry site (IRES), ZsGreen, a green fluorescent protein, woodchuck hepatitis virus post-transcriptional regulatory element (WPRE), and simian virus 40 origin (SV40). Constitutive expression of the transgene comprising of a CD8 leader sequence, an scFV specific to Lym-2, a CD8 hinge and transmembrane region and CD28, 4-1BB and CD3ζ signaling domain, is insured by the presence of the EF-1α promoter. Expression of the detection protein, ZsGreen is carried out by the IRES region. Integration of the vector can be assayed by the presence of ZsGreen in the cells, via fluorescent microscopy.

Analysis of the Lym-1 CAR T-cells for expression of the Lym-1 CAR, showed 62.5% of the transduced T-cells positive for Lym-1 (FIG. 8 middle panel). In contrast, only 1% of the un-transduced T-cells used as a control were positive for CAR expression (FIG. 8 left panel). CD19 transduced T-cells were used as a positive control and showed 52% expression of the CD19 CAR (FIG. 8 right panel).

Cytotoxicity for Lym-1 CAR T-Cells

The cytolytic activity of the Lym-1 CAR T-cells was examined using Raji, a B-cell lymphoma cell line. Raji expresses the Lym-1 antigen (HLA-Dr10), as determined by FACS analysis. Lym-1 CAR T-cells were added to the Raji cells in ratios of 20:1, 10:1, 5:1 and 1:1 of effector to target cells. Lym-1 CAR T-cells showed increased lysis of the target Raji cells at ratios of 5:1, 10:1 and 20:1 with a lysis rate of 22%. In comparison, untransduced T-cells did not lyse Raji cells at any of the ratios tested.

Example 4—Lym-2 CAR Cells

Construction of the CAR Lentiviral Constructs

The Lym-2 CAR vector contains a CD8 leader sequence followed by the extracellular antigen binding moiety or scFV, which binds specifically to the Lym-2 antigen (HLA-Dr). The scFV is connected via a CD8 hinge region to the cytoplasmic signaling domain, comprised of the CD8 transmembrane region, and the signaling domains from 4-1BB and CD3ζ. The CAR sequence including the signaling domains, were synthetically synthesized by Genewiz Gene Synthesis services (Piscataway, N.J.). The plasmids are purified and digested with the appropriate restriction enzymes to be inserted into an HIV-1-based lentiviral vector (pLVX-IRES-ZsGreen, Clontech, Signal Hill, Calif.) containing HIV-1 5' and 3' long terminal repeats (LTRs), packaging signal (Ψ), EF1α promoter, internal ribosome entry site (IRES), woodchuck hepatitis virus post-transcriptional regulatory element (WPRE) and simian virus 40 origin (SV40) via overnight $T_4$ DNA ligase reaction (New England Biosciences; Ipswich, Mass.), followed by deletion of the IRES-ZsGreen using restriction enzyme digestion and ligation with $T_4$ DNA ligase. NovaBlue Singles™ chemically-competent *E. coli* cells are then transformed with the resulting CAR-containing lentiviral plasmid.

Production of Lentiviral Particles

Prior to transfection, HEK 293T cells are seeded at $4.0 \times 10^6$ cells in a 150 cm$^2$ tissue-culture-treated flask in 20 mL DMEM supplemented with 10% dialyzed FCS and incubated overnight at 37° C. in a humidified 5% CO$_2$ incubator. Once 80-90% confluent, HEK 293T cells are incubated in 20 ml DMEM supplemented with 1-% dialyzed FCS without penicillin/streptamycin for two hours in a 37° C. humidified 5% CO$_2$ incubator. HEK293T cells are co-transfected with the CAR plasmid and lentiviral packaging plasmids containing genes necessary to form the lentiviral envelope & capsid components. A proprietary reaction buffer and polymer to facilitate the formation of plasmid-containing nanoparticles that bind HEK 293T cells are also added. After incubating the transfected-HEK 293T cell cultures for 24 hours at 37° C., the transfection medium is replaced with 20 mL fresh complete DMEM. Lentivirus supernatants are collected every 24 hours for 3 days and the supernatants are centrifuged at 1,250 rpm for 5 mins at 4° C., followed by filter sterilization and centrifugation in an ultracentrifuge at 20,000 g for 2 hrs at 4° C. The concentrated lentivirus is re-suspended in PBA containing 7% trehalose and 1% BSA. The lentivirus is aliquoted and stored at −80° C. until use for transduction of target CD4$^+$ and CD8$^+$ T cells. The cell supernatants harvested after 24 hours are tested for lentiviral particles via a sandwich ELISA against p24, the main lentiviral capsid protein. Transfection efficiency was estimated between 20%-50%, by staining with a biotin-labeled Protein L antibody (Genscript, Piscataway, N.J.), followed by incubation with a streptavidin conjugated to PE, and detection by FACS analysis.

Purification, Activation, and Enrichment of Human CD4$^+$ and CD8$^+$ Peripheral Blood T-Cells Peripheral blood mononuclear cells (PBMCs) enriched by density gradient centrifugation with Ficoll-Paque Plus (GE Healthcare; Little Chalfont, Buckinghamshire, UK) are recovered and washed by centrifugation with PBS containing 0.5% bovine serum albumin (BSA) and 2 mM EDTA. T-cell enrichment kits (Stem Cell Technologies) are used to isolate these human T-cell subsets magnetically using negative selection for CD4$^+$ and CD8$^+$ T-cells. The purity of CD4$^+$ and CD8$^+$ T-cell populations is assessed by flow cytometry using Life Technologies Acoustic Attune® Cytometer, and will be enriched by Fluorescence-Activated Cell Sorting. CD4$^+$ and CD8$^+$ T-cells mixed 1:1 are maintained at a density of $1.0 \times 10^6$ cells/mL in complete 50% Click's medium/50% RPMI-1640 medium supplemented with 100 IU/mL IL-2 in a suitable cell culture vessel, to which α-CD3/α-CD28 Human T-cell activator beads (Stem Cell Technologies) are added to activate cultured T cells. T-cells are then incubated at 37° C. in a 5% CO$_2$ humidified incubator for 2 days prior to transduction with CAR lentiviral particles.

Lentiviral Transduction of CD4$^+$ CD8$^+$ T-Cells

Activated T-cells are collected and dead cells removed by Ficoll-Hypaque density gradient centrifugation or the use of MACS Dead Cell Removal Kit (Miltenyi Biotec; San Diego, Calif.). In a 6-well plate, activated T-cells are plated at a concentration of $1.0 \times 10^6$ cells/mL in complete medium. Cells are transduced with the lentiviral particles supplemented with Lentiblast, a transfection aid (Oz Biosciences, San Diego, Calif.) to the cells. Transduced cells are incubated for 24 hours at 37° C. in a 37° C. humidified 5% CO$_2$ incubator. The cells are spun down and the media changed, followed by addition of the T-cell activator beads (Stem Cell Technologies, San Diego, Calif.).

Cell Cytotoxicity Assays

Cytotoxicity of the Lym-2 CAR T-cells are determined using the lactate dehydrogenase (LDH) cytotoxicity kit (Thermo Scientific, Carlsbad, Calif.). Activated T-cells are collected and $1 \times 10^6$ cells are transduced with the Lym-2 CAR lentiviral construct as described above. Cells are activated used the T-cell activator beads (Stem Cell Technologies, San Diego, Calif.) for two days prior to cytotoxicity assays. The optimal number of target cells will be determined as per the manufacturer's protocol. For the assays, the appropriate target cells will be plated in triplicate in a 96 well plate for 24 hours at 37° C. in a 37° C. humidified 5% CO$_2$ incubator, followed by addition of activated CAR T-cells in ratios of 20:1, 10:1, 5:1 and 1:1, and incubated for 24 as above. Cells will be lysed at 37° C. for 45 mins and centrifuged at 1,250 rpm for 5 minutes. The supernatants are transferred to a fresh 96 well plate, followed by the addition of the reaction mixture for 30 minutes. The reaction is stopped using the stop solution and the plate read at 450 nm with an absorbance correction at 650 nm.

In Vivo Tumor Regression Assay

Foxn1 null mice are injected with immortalized B lymphoma cell line, Raji, which expresses the Lym-2 antigen. Two$\times 10^6$ Raji cells with $1 \times 10^6$ human fibroblasts in 200 ul of phosphate buffered saline (PBS) are injected into the left flank of the pre-irradiated (400 rads) BALB/c mice in insure a high take rate of tumor. T-cells are activated for 2 days with the αCD3/CD28 activator complex (Stem Cell Technologies, San Diego, Calif.). The activated T-cells are then transduced with Lym-2 CAR lentiviral particles, followed by activation with the αCD3/CD28 activator complex for an additional 2 days. The activated T-cells expressing the Lym-2 CAR ($2.5 \times 10^6$) are injected intravenously into the mice on day 7 after tumor inoculation. Tumor sizes are assessed 3×/week using Vernier calipers and the tumor volumes calculated.

Detection of Lym-2 CAR Expression

Figure 11:
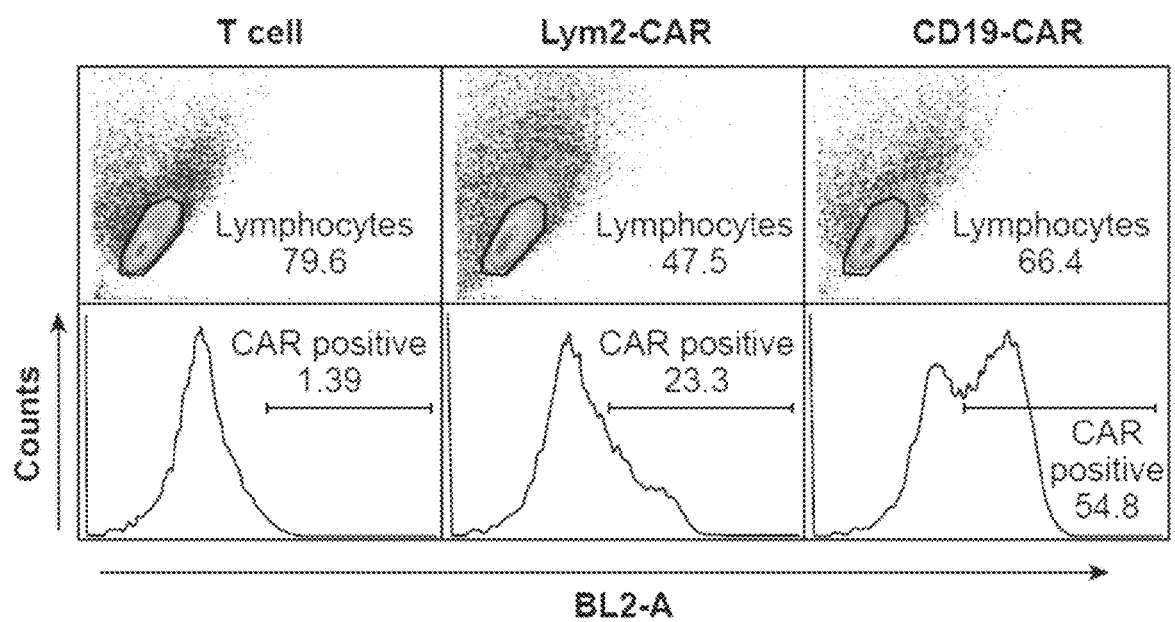
FIG. 11 shows expression of Lym-2 CAR on primary human T-cells. T-cells were transduced with the Lym-2 CAR and stained with Biotein-Protein L, followed by Streptavidin-PE. Cells were analyzed by flow cytometry.
Figure 12:
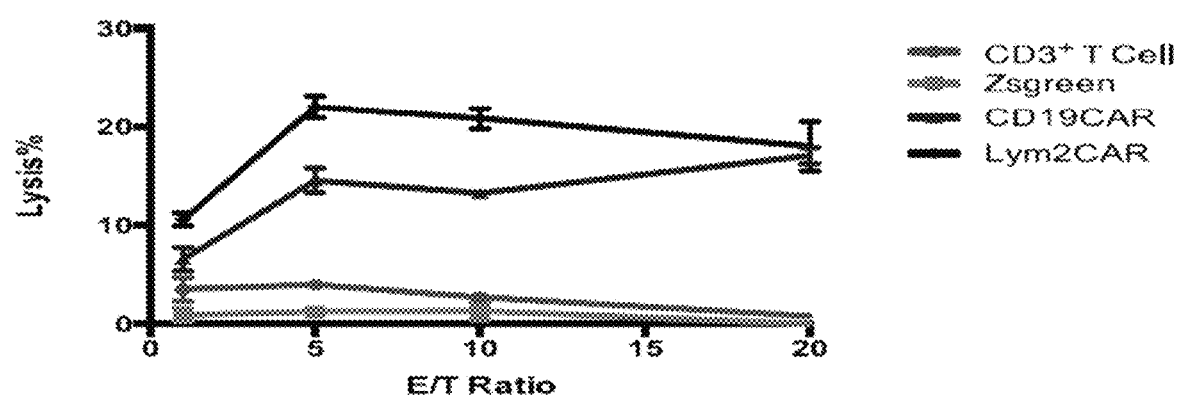
FIG. 12 shows cytotoxicity of the Lym-2-CAR T-cells. Cytotoxicity of the Lym-2 CAR expressing T-cells was determined using an LDH cytotoxicity kit as described in the Methods. Prior to the assay, T-cells were activated using αCD3/CD8 beads (Stem Cell Technologies, 30 ul to 2 ml of media). The activated T-cells were transduced with Lym-2 CAR lentiviral particles, following which the T cells were activated using the αCD3/CD8 beads. Un-transduced, activated T-cells were used as a control. 15,000 Raji cells were plated per well. Lym-2 CAR transduced T cells were added in ratios of 20:1, 10:1, 5:1 and 1:1 to the wells. Each data point represents the average of triplicate measurements.
Figure 13:
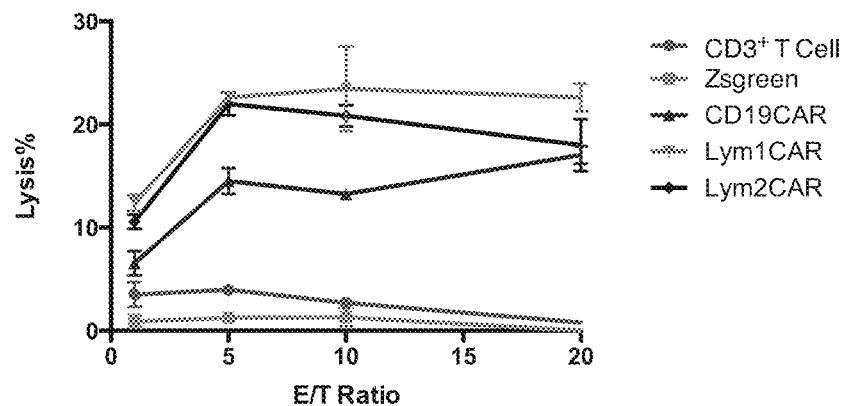
FIG. 13 demonstrates that Lym-1, Lym-2, and CD19 CAR T-cells are highly cytotoxic to human lymphoma Raji cells. Raji Burkitt's lymphoma cells are positive for both HLA-Dr targeted by Lym-1 and Lym-2 and also CD19 which acted as a positive control for CD19 CAR T-cells. Negative controls consisted of CD3+ T cells and Zsgreen cells.
Figure 14:
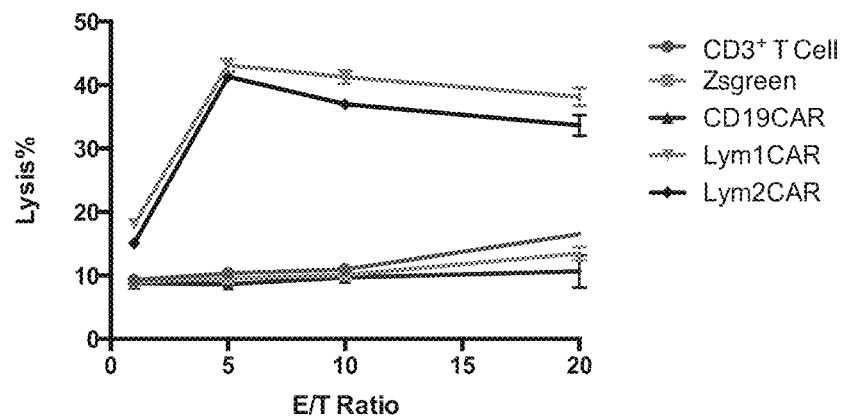
FIG. 14 demonstrates that Lym-1, Lym-2, but not CD19 CAR are highly cytolytic against HLA-Dr positive but CD19 negative TLBR-2 human T lymphoma cells in vitro. TLBR-2 human T-lymphoma cells derived from a breast implant associated lymphoma is positive for HLA-Dr but not CD19 (Lechner et al. (2012) Clin. Cancer Res. 18 (17):4549-4559). These results demonstrate the specificity of the Lym-1 and Lym-2 CAR T-cells and their potency in killing HLA-Dr positive tumors. The percentage of Lym-1 CAR-T and CD19 CAR-T positive cells were adjusted to 50% using regular un-transduced primary T cells. The percentage of Lym-2 CAR-T cells was 24%.

Analysis of the Lym-2 CAR T-cells for expression of the Lym-1 CAR, showed 28% of the transduced T-cells positive for Lym-2 (FIG. 11 middle panel). In contrast, only 1% of the un-transduced T-cells used as a control were positive for CAR expression (FIG. 11 left panel). CD19 transduced T-cells were used as a positive control and showed 52% expression of the CD19 CAR (FIG. 11 right panel).

Cytotoxicity for Lym-2 CAR T-Cells

The cytolytic activity of the Lym-2 CAR T-cells was determined using Raji, a B-cell lymphoma cell line. Raji expresses the Lym-2 antigen, as determined by FACS analysis. Lym-2 CAR T-cells were added to the Raji cells in ratios of 20:1, 10:1, 5:1 and 1:1 of effector to target cells. Lym-2 CAR T-cells show increased lysis of the target Raji cells at ratios of 5:1 and 10:1 with a lysis rate of 22%. In comparison, untransduced T-cells did not lyse Raji cells at any of the ratios tested.

Example 5—NK Cell Transduction

NK-92MI Transduction

Figure 15:
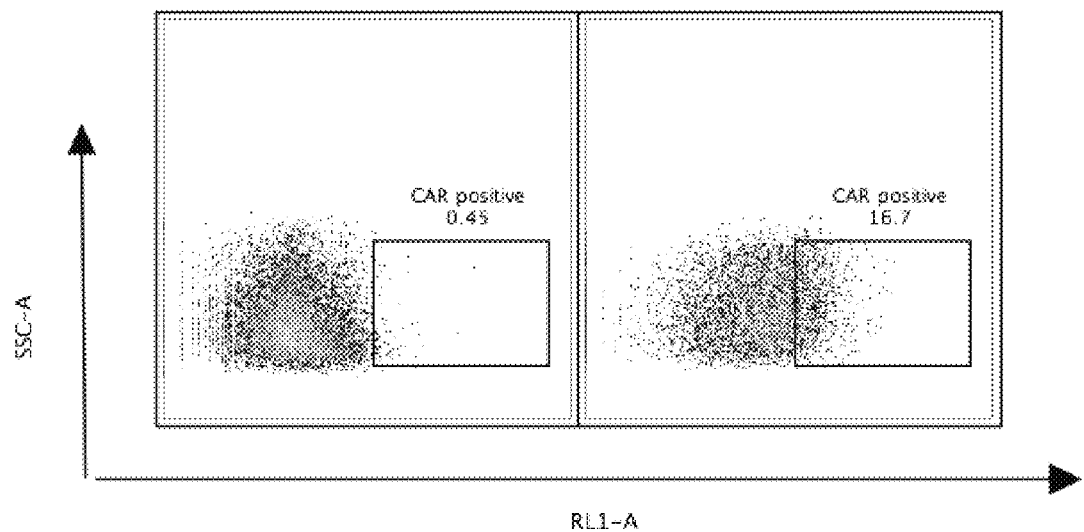
FIG. 15 shows the results of FACs analysis of transfected NK cells.
Figure 15:
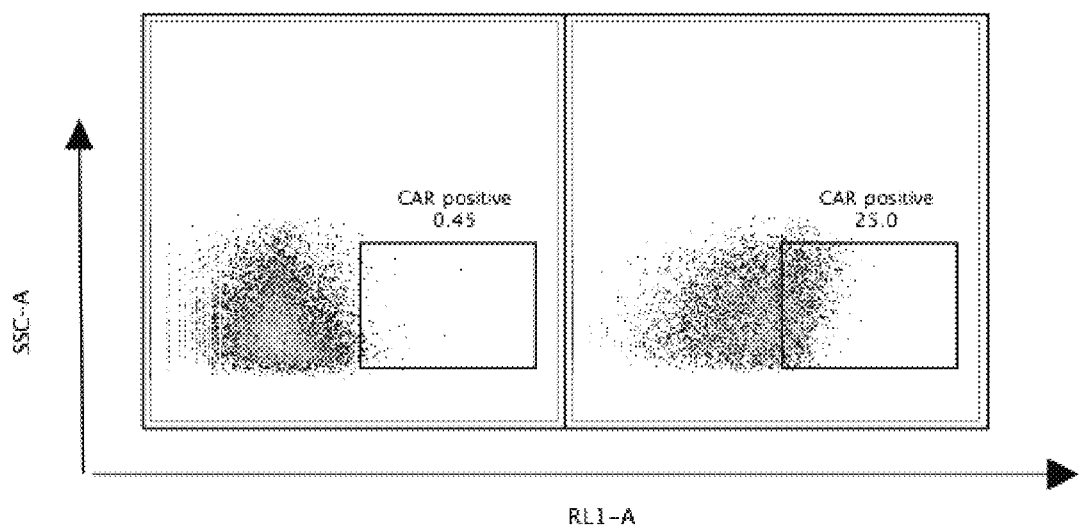

NK-92Mi cell line was purchased from ATCC (CRL-2408) and maintained in RPMI-1640 with 10% FBS. Before transduction, non-tissue treated 24-wells were incubated with 10 μg RetroNectin (Clontech T100A) in 300 μL Phosphate Buffered Saline (PBS) at room temperature for 2 hours. One million NK-92Mi cells and lentivirus (MOI=5) were mixed and added to the RetroNectin coated plates. The plates were then centrifuged at 28° C. 800 g for 90 min. After centrifugation, the cells were maintained in a cell culture incubator overnight. After incubation, the cells were washed with PBS three times the following morning and the transduced NK-92Mi cells were then transferred to 24 well G-Rex (Wilson Wolf) plates for expansion. Seven days after Lentivirus transduction, the cells were washed 3× in wash buffer (4% BSA in PBS), stained with Biotein-Protein L (1 ug/1 million cells. Genscript) at 4° C. for 45 min, and washed 3× with wash buffer before adding 2 ul Streptavidin-APC (BD science) at 4° C. for 45 min. After a final 3 washes in wash buffer, the cells were analyzed by FACs (Attune) (FIG. 15).

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

The invention claimed is:

1. A chimeric antigen receptor (CAR) comprising: (a) an antigen binding domain of an anti-HLA-DR antibody; (b) a CD8 α hinge domain; (c) a CD8 α transmembrane domain; (d) a CD28 costimulatory signaling region and/or a 4-1BB costimulatory signaling region; and (e) a CD3 zeta signaling domain, wherein the antigen binding domain of an anti-HLA-DR antibody comprises:
   (i) a heavy chain variable region comprising SEQ ID NO: 8 and a light chain variable region comprising SEQ ID NO: 18; or
   (ii) a heavy chain variable region comprising SEQ ID NO: 10 and a light chain variable region comprising SEQ ID NO: 20.

2. An isolated complex comprising the CAR of claim 1 bound to a cell expressing HLA-DR.

3. An isolated nucleic acid sequence encoding the CAR of claim 1 or its complement or an equivalent of each thereof.

4. A vector comprising the isolated nucleic acid sequence of claim 3.

5. An isolated cell comprising the CAR of claim 1.

6. A complex comprising the isolated cell of claim 5 bound to a cell expressing HLA-DR.

7. A composition comprising a carrier and the isolated cell of claim 5.

8. A method of inhibiting the growth of a tumor or treating a cancer that overexpresses HLA-DR as compared to a normal, non-cancerous counterpart cell in a subject in need thereof, comprising administering to the subject an effective amount of the isolated cell of claim 5.

9. The method of claim 8, wherein the isolated cells are autologous or allogeneic to the subject being treated.

10. The method of claim 8, further comprising administering to the subject an anti-tumor therapy other than the HLA-DR CAR therapy.

11. The isolated cell of claim 5, wherein the isolated cell is a T-cell or an NK-cell.

12. The method of claim 8, wherein the isolated cell is a T-cell or an NK-cell.

13. The method of claim 8, wherein the tumor is cancerous.

14. The method of claim 8, wherein the subject is a mammal.

15. The method of claim 8, wherein the tumor or cancer is a B-cell lymphoma tumor or a leukemia tumor.

16. The method of claim 8, wherein the isolated cells are administered as a therapy of the group of: a first line, a second line, a third line, a fourth line or a fifth line therapy.

* * * * *

SEQUENCE LISTING

```
<160> NUMBER OF SEQ ID NOS: 52

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Ser Leu Thr Ser Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Ser Asn Tyr Trp
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Trp Ser Asp Gly Ser Thr
1               5
```

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Arg Phe Lys Ser His Asn Tyr Ala Thr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ser His Tyr Gly Ser Thr Leu Ala Phe Ala Ser
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Arg Arg Ile Gly Asn Ser Asp Tyr Asp Trp Trp Tyr Phe Asp Val
1               5                   10                  15

<210> SEQ ID NO 7
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
caggtgcagc tgaaggagtc aggacctggc ctggtggcgc cctcacagag cctgtccatc     60
acatgcacca tctcagggtt ctcattaacc agctatggtg tacactgggt tcgccagcct    120
ccaggaaagg gtctggagtg gctggtagtg atatggagtg atggaagcac aacctataat    180
tcagctctca aatccagact gagcatcagc aaggacaact ccaagagcca agttttctta    240
aaaatgaaca gtctccaaac tgatgacaca gccatatact actgtgccag tcactacggt    300
agtaccctta cctttgcttc ctggggccac gggactctgg tcactgtctc tgca          354

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Leu Lys Glu Ser Gly Pro Gly Leu Val Ala Pro Ser Gln Ser Leu
1               5                   10                  15

Ser Ile Thr Cys Thr Ile Ser Gly Phe Ser Leu Thr Ser Tyr Gly Val
            20                  25                  30

His Trp Val Arg Gln Pro Pro Gly Lys Gly Leu Glu Trp Leu Val Val
        35                  40                  45

Ile Trp Ser Asp Gly Ser Thr Thr Tyr Asn Ser Ala Leu Lys Ser Arg
    50                  55                  60

Leu Ser Ile Ser Lys Asp Asn Ser Lys Ser Gln Val Phe Leu Lys Met
65                  70                  75                  80

Asn Ser Leu Gln Thr Asp Asp Thr Ala Ile Tyr Tyr Cys Ala Ser His
                85                  90                  95

Tyr Gly Ser Thr Leu Ala Phe Ala Ser Trp Gly His Gly Thr Leu Val
            100                 105                 110

Thr Val Ser Ala
        115

<210> SEQ ID NO 9
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaagtgcagc ttgaggagtc tggaggaggc ttggtgcaac ctggaggctc catgaaactc    60
tcctgtgttg cctctggatt cactttcagt aactattgga tgaactgggt ccgccagtct   120
ccagagaagg ggcttgagtg ggttgctgaa attagattta atctcataa ttatgcaaca    180 cattttgcgg agtctgtgaa agggaggttc accatctcaa gagatgattc caaaagtagt   240
gtctacctgc aaatgaacaa cttaagagct gaagacactg gcatttatta ctgtaccagg   300
aggataggaa actctgatta cgactggtgg tacttcgatg tctggggcgc agggacctca   360
gtcaccgtct cctcagctag c                                             381

<210> SEQ ID NO 10
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Phe Lys Ser His Asn Tyr Ala Thr His Phe Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Arg Arg Ile Gly Asn Ser Asp Tyr Asp Trp Trp Tyr Phe
            100                 105                 110

Asp Val Trp Gly Ala Gly Thr Ser Val Thr Val Ser Ser Ala Ser
            115                 120                 125

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Asn Ile Tyr Ser Tyr
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Asn Val Gly Asn Asn
1               5

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Ala Lys
1

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ala Ser
1

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln His His Tyr Gly Thr Phe Thr
1               5

<210> SEQ ID NO 16
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 16

Gln Gln Tyr Asn Thr Tyr Pro Phe Thr
1               5

<210> SEQ ID NO 17
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gacatccaga tgactcagtc tccagcctcc ctatctgcat ctgtgggaga aactgtcacc      60
atcatatgtc gagcaagtgt gaatatttac agttatttag catggtatca gcagaaacag    120
ggaaaatctc ctcagctcct ggtctataat gccaaaatct tagcagaagg tgtgccatca    180
aggttcagtg gcagtggatc aggcacacag ttttctctga agatcaacag cctgcagcct    240
gaagattttg ggagttatta ctgtcaacat cattatggta cattcacgtt cggctcgggg    300
acaaagttgg aaataaaa                                                  318

<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ala Ser Leu Ser Ala Ser Val Gly
1               5                   10                  15

Glu Thr Val Thr Ile Ile Cys Arg Ala Ser Val Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Ile Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Phe Thr
                85                  90                  95

Phe Gly Ser Gly Thr Lys Leu Glu Ile Lys
            100                 105

<210> SEQ ID NO 19
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gacattgtga tgacccagtc tcacaaattc atgtccacat cagtaggaga cagggtcagc      60
gtcacctgca aggccagtca gaatgtgggt aataatgtag cctggtatca acagaaacca    120
gggcaatctc ctaaagtact gatttactcg gcatcctacc ggtacagtgg agtccctgat    180

```
cgcttcacag gcagtggatc tgggacagat ttcactctca ccatcagtaa tgtgcagtct    240
gaagacttgg cagagtattt ctgtcagcaa tataacacct atccattcac gttcggctcg    300
gggacaaagt tggaaataaa a                                              321
```

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Asp Ile Val Met Thr Gln Ser His Lys Phe Met Ser Thr Ser Val Gly
1               5                   10                  15

Asp Arg Val Ser Val Thr Cys Lys Ala Ser Gln Asn Val Gly Asn Asn
            20                  25                  30

Val Ala Trp Tyr Gln Gln Lys Pro Gly Gln Ser Pro Lys Val Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Thr Tyr Pro Phe
                85                  90                  95

Thr Phe Gly Ser Gly Thr Lys Leu Glu Ile Lys
            100                 105
```

<210> SEQ ID NO 21
<211> LENGTH: 384
<212> TYPE: PRT
<213> ORGANISM: Homo sapiens

<400> SEQUENCE: 21

```
Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175
```

```
Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Val Glu Glu Gly Leu Leu Glu Arg His Ser
210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
            290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
            325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380

<210> SEQ ID NO 22
<211> LENGTH: 330
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                    165                 170                 175
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 326
<212> TYPE: PRT
<213> ORGANISM: Homo sapiens

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 24
<211> LENGTH: 377
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 25
<211> LENGTH: 452
<212> TYPE: PRT
<213> ORGANISM: Homo sapiens

<400> SEQUENCE: 25

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr

-continued

```
                245                 250                 255
Ile Ser Trp Thr Arg Gln Asn Gly Glu Ala Val Lys Thr His Thr Asn
            260                 265                 270
Ile Ser Glu Ser His Pro Asn Ala Thr Phe Ser Ala Val Gly Glu Ala
        275                 280                 285
Ser Ile Cys Glu Asp Asp Trp Asn Ser Gly Glu Arg Phe Thr Cys Thr
    290                 295                 300
Val Thr His Thr Asp Leu Pro Ser Pro Leu Lys Gln Thr Ile Ser Arg
305                 310                 315                 320
Pro Lys Gly Val Ala Leu His Arg Pro Asp Val Tyr Leu Leu Pro Pro
                325                 330                 335
Ala Arg Glu Gln Leu Asn Leu Arg Glu Ser Ala Thr Ile Thr Cys Leu
            340                 345                 350
Val Thr Gly Phe Ser Pro Ala Asp Val Phe Val Gln Trp Met Gln Arg
        355                 360                 365
Gly Gln Pro Leu Ser Pro Glu Lys Tyr Val Thr Ser Ala Pro Met Pro
    370                 375                 380
Glu Pro Gln Ala Pro Gly Arg Tyr Phe Ala His Ser Ile Leu Thr Val
385                 390                 395                 400
Ser Glu Glu Glu Trp Asn Thr Gly Glu Thr Tyr Thr Cys Val Ala His
                405                 410                 415
Glu Ala Leu Pro Asn Arg Val Thr Glu Arg Thr Val Asp Lys Ser Thr
            420                 425                 430
Gly Lys Pro Thr Leu Tyr Asn Val Ser Leu Val Met Ser Asp Thr Ala
        435                 440                 445
Gly Thr Cys Tyr
    450
```

<210> SEQ ID NO 26
<211> LENGTH: 327
<212> TYPE: PRT
<213> ORGANISM: Homo sapiens

<400> SEQUENCE: 26

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 27
<211> LENGTH: 353
<212> TYPE: PRT
<213> ORGANISM: Homo sapiens

<400> SEQUENCE: 27

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205
```

```
Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 28
<211> LENGTH: 340
<212> TYPE: PRT
<213> ORGANISM: Homo sapiens

<400> SEQUENCE: 28

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220
```

```
Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
                275                 280                 285

Ala Glu Asp Trp Lys Lys Gly Asp Thr Phe Ser Cys Met Val Gly His
        290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 29
<211> LENGTH: 106
<212> TYPE: PRT
<213> ORGANISM: Homo sapiens

<400> SEQUENCE: 29

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 30
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Asp Thr Arg Pro Arg Phe Leu Glu Glu Val Lys Phe Glu Cys His
1               5                   10                  15

Phe Phe Asn Gly Thr Glu Arg Val Arg Leu Leu Glu Arg Arg Val His
            20                  25                  30

Asn Gln Glu Glu Tyr Ala Arg Tyr Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Arg Arg Arg Ala Ala Val Asp Thr Tyr Cys Arg
65                  70                  75                  80
```

His Asn Tyr Gly Val Gly Glu Ser Phe Thr Val Gln Arg Arg Val Gln
                85                  90                  95

Pro Lys Val Thr Val Tyr Pro Ser Lys Thr Gln Pro Leu Gln His His
            100                 105                 110

Asn Leu Leu Val Cys Ser Val Asn Gly Phe Tyr Pro Gly Ser Ile Glu
        115                 120                 125

Val Arg Trp Phe Arg Asn Gly Gln Glu Glu Lys Thr Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Gln Ser Gly Glu Val Tyr Thr Cys Gln Val Glu
                165                 170                 175

His Pro Ser Val Met Ser Pro Leu Thr Val Glu Trp Arg Ala Arg Ser
            180                 185                 190

Glu Ser Ala Gln Ser Lys Met Leu Ser Gly Val Gly Gly Phe Val Leu
        195                 200                 205

Gly Leu Leu Phe Leu Gly Ala Gly Leu Phe Ile Tyr Phe Arg Asn Gln
    210                 215                 220

Lys Gly His Ser Gly Leu Pro Pro Thr Gly Phe Leu Ser
225                 230                 235

<210> SEQ ID NO 31
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Asp Thr Arg Pro Arg Phe Leu Glu Leu Leu Lys Ser Glu Cys His
1               5                   10                  15

Phe Phe Asn Gly Thr Glu Arg Val Arg Phe Leu Glu Arg His Phe His
            20                  25                  30

Asn Gln Glu Glu Tyr Ala Arg Phe Asp Ser Asp Val Gly Glu Tyr Arg
        35                  40                  45

Ala Val Phe Glu Leu Gly Arg Pro Asp Ala Glu Tyr Trp Asn Ser Gln
    50                  55                  60

Lys Asp Leu Leu Glu Gln Lys Arg Gly Gln Val Asp Asn Tyr Cys Arg
65                  70                  75                  80

His Asn Tyr Gly Val Val Glu Ser Phe Thr Val Gln Arg Arg Val His
                85                  90                  95

Pro Gln Val Thr Val Tyr Pro Ala Lys Thr Gln Pro Leu Gln His His
            100                 105                 110

Asn Leu Leu Val Cys Ser Val Ser Gly Phe Tyr Pro Gly Ser Ile Glu
        115                 120                 125

Val Arg Trp Phe Arg Asn Gly Gln Glu Glu Lys Ala Gly Val Val Ser
    130                 135                 140

Thr Gly Leu Ile Gln Asn Gly Asp Trp Thr Phe Gln Thr Leu Val Met
145                 150                 155                 160

Leu Glu Thr Phe Pro Arg Ser Gly Glu Val Tyr Thr Cys Gln Val Glu
                165                 170                 175

His Pro Ser Val Thr Ser Pro Leu Thr Val Glu Trp Ser Ala Arg Ser
            180                 185                 190

Glu Ser Ala Gln Ser Lys Met Leu Ser Gly Val Gly Gly Phe Val Leu

```
                    195                 200                 205
Gly Leu Leu Phe Leu Gly Ala Gly Leu Phe Ile Tyr Phe Arg Asn Gln
        210                 215                 220
Lys Gly His Ser Gly Leu Gln Pro Thr Gly Phe Leu Ser
225                 230                 235

<210> SEQ ID NO 32
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Asp Thr Arg Pro Arg Phe Leu Glu Tyr Ser Thr Ser Glu Cys His
1               5                   10                  15

Phe Phe Asn Gly Thr Glu Arg Val Arg Tyr Leu Asp Arg Tyr Phe His
            20                  25                  30

Asn Gln Glu Glu Asn Val Arg Phe Asp Ser Asp Val Gly Glu Phe Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Gly Arg Val Asp Asn Tyr Cys Arg
65                  70                  75                  80

His Asn Tyr Gly Val Val Glu Ser Phe Thr Val Gln Arg Arg Val His
                85                  90                  95

Pro Lys Val Thr Val Tyr Pro Ser Lys Thr Gln Pro Leu Gln His His
            100                 105                 110

Asn Leu Leu Val Cys Ser Val Ser Gly Phe Tyr Pro Gly Ser Ile Glu
        115                 120                 125

Val Arg Trp Phe Arg Asn Gly Gln Glu Glu Lys Thr Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Val Thr Ser Pro Leu Thr Val Glu Trp Arg Ala Arg Ser
            180                 185                 190

Glu Ser Ala Gln Ser Lys Met Leu Ser Gly Val Gly Gly Phe Val Leu
        195                 200                 205

Gly Leu Leu Phe Leu Gly Ala Gly Leu Phe Ile Tyr Phe Arg Asn Gln
    210                 215                 220

Lys Gly His Ser Gly Leu Gln Pro Arg Gly Phe Leu Ser
225                 230                 235

<210> SEQ ID NO 33
<211> LENGTH: 51
<212> TYPE: PRT
<213> ORGANISM: Homo sapiens

<400> SEQUENCE: 33

Pro Ala Lys Pro Thr Thr Thr Pro Ala Pro Arg Pro Pro Thr Pro Ala
1               5                   10                  15

Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala Cys
```

```
                35                  40                  45

Asp Ile Tyr
    50

<210> SEQ ID NO 34
<211> LENGTH: 49
<212> TYPE: PRT
<213> ORGANISM: Mus musculus

<400> SEQUENCE: 34

Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp Ile
        35                  40                  45

Tyr

<210> SEQ ID NO 35
<211> LENGTH: 51
<212> TYPE: PRT
<213> ORGANISM: Felis catus

<400> SEQUENCE: 35

Pro Val Lys Pro Thr Thr Thr Pro Ala Pro Arg Pro Pro Thr Gln Ala
1               5                   10                  15

Pro Ile Thr Thr Ser Gln Arg Val Ser Leu Arg Pro Gly Thr Cys Gln
            20                  25                  30

Pro Ser Ala Gly Ser Thr Val Glu Ala Ser Gly Leu Asp Leu Ser Cys
        35                  40                  45

Asp Ile Tyr
    50

<210> SEQ ID NO 36
<211> LENGTH: 21
<212> TYPE: PRT
<213> ORGANISM: Homo sapiens

<400> SEQUENCE: 36

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 37
<211> LENGTH: 21
<212> TYPE: PRT
<213> ORGANISM: Mus musculus

<400> SEQUENCE: 37

Ile Trp Ala Pro Leu Ala Gly Ile Cys Val Ala Leu Leu Leu Ser Leu
1               5                   10                  15

Ile Ile Thr Leu Ile
            20

<210> SEQ ID NO 38
<211> LENGTH: 21
<212> TYPE: PRT
<213> ORGANISM: Rattus norvegicus

<400> SEQUENCE: 38
```

Ile Trp Ala Pro Leu Ala Gly Ile Cys Ala Val Leu Leu Ser Leu
1               5                   10                  15

Val Ile Thr Leu Ile
            20

<210> SEQ ID NO 39
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 40
<211> LENGTH: 220
<212> TYPE: PRT
<213> ORGANISM: Unknown
<220> FEATURE:
<223> OTHER INFORMATION: Description of Unknown:
      CD28 sequence

<400> SEQUENCE: 40

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 41
<211> LENGTH: 112
<212> TYPE: PRT
<213> ORGANISM: Unknown
<220> FEATURE:
<223> OTHER INFORMATION: Description of Unknown:
    CD3 zeta signaling domain

<400> SEQUENCE: 41

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 42
<211> LENGTH: 48
<212> TYPE: DNA
<213> ORGANISM: Unknown
<220> FEATURE:
<223> OTHER INFORMATION: Description of Unknown:
    IgG1 heavy chain hinge sequence

<400> SEQUENCE: 42
ctcgagccca aatcttgtga caaaactcac acatgcccac cgtgcccg                 48

<210> SEQ ID NO 43
<211> LENGTH: 81
<212> TYPE: DNA
<213> ORGANISM: Unknown
<220> FEATURE:
<223> OTHER INFORMATION: Description of Unknown:
    CD28 transmembrane region

<400> SEQUENCE: 43
ttttgggtgc tggtggtggt tggtggagtc ctggcttgct atagcttgct agtaacagtg    60
gcctttatta ttttctgggt g                                              81

<210> SEQ ID NO 44
<211> LENGTH: 126
<212> TYPE: DNA
<213> ORGANISM: Unknown
<220> FEATURE:
<223> OTHER INFORMATION: Description of Unknown:
    4-1BB co-stimulatory signaling region

<400> SEQUENCE: 44
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

```
<210> SEQ ID NO 45
<211> LENGTH: 123
<212> TYPE: DNA
<213> ORGANISM: Unknown
<220> FEATURE:
<223> OTHER INFORMATION: Description of Unknown:
      CD28 co-stimulatory signaling region

<400> SEQUENCE: 45
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 46
<211> LENGTH: 339
<212> TYPE: DNA
<213> ORGANISM: Unknown
<220> FEATURE:
<223> OTHER INFORMATION: Description of Unknown:
      CD3 zeta signaling region

<400> SEQUENCE: 46
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240
cggaggggca gggggcacga tggcctttac cagggtctca gtacagccac caaggacacc   300
tacgacgccc ttcacatgca ggccctgccc cctcgctaa                          339

<210> SEQ ID NO 47
<211> LENGTH: 105
<212> TYPE: DNA
<213> ORGANISM: Unknown
<220> FEATURE:
<223> OTHER INFORMATION: Description of Unknown:
      ICOS costimulatory signaling region

<400> SEQUENCE: 47
acaaaaaaga agtattcatc cagtgtgcac gaccctaacg gtgaatacat gttcatgaga    60
gcagtgaaca cagccaaaaa atccagactc acagatgtga cccta                   105

<210> SEQ ID NO 48
<211> LENGTH: 108
<212> TYPE: DNA
<213> ORGANISM: Unknown
<220> FEATURE:
<223> OTHER INFORMATION: Description of Unknown:
      OX40 costimulatory signaling region

<400> SEQUENCE: 48
agggaccaga ggctgccccc cgatgcccac aagccccctg ggggaggcag tttccggacc    60
cccatccaag aggagcaggc cgacgcccac tccaccctgg ccaagatc                108

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49
```

```
Gly Gly Gly Gly Ser Gly Gly Gly Gly Ser Gly Gly Gly Gly
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Phe Gly Ala Gly Leu Val Leu Gly Gly Gln Phe Met
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Gly Gly Ser Gly Gly Gly Gly Ser Gly Gly Gly Gly Ser
1               5                   10                  15

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Gly Gly Ser
1               5
```